(12) United States Patent
Heisler et al.

(10) Patent No.: US 9,486,232 B2
(45) Date of Patent: Nov. 8, 2016

(54) ENDOSCOPIC CUTTING INSTRUMENTS HAVING IMPROVED EFFICIENCY AND REDUCED MANUFACTURING COSTS

(71) Applicant: Hanshi LLC, Brazoria, TX (US)

(72) Inventors: Gary R. Heisler, Brazoria, TX (US); Robert A. Van Wyk, St. Pete Beach, FL (US)

(73) Assignee: HANSHI LLC, Brazoria, TX (US)

( * ) Notice: Subject to any disclaimer, the term of this patent is extended or adjusted under 35 U.S.C. 154(b) by 250 days.

(21) Appl. No.: 14/224,568

(22) Filed: Mar. 25, 2014

(65) Prior Publication Data

US 2014/0324086 A1    Oct. 30, 2014

Related U.S. Application Data

(60) Provisional application No. 61/852,956, filed on Mar. 25, 2013, provisional application No. 61/958,750, filed on Aug. 5, 2013.

(51) Int. Cl.
*A61B 17/32* (2006.01)
*A61B 17/00* (2006.01)

(52) U.S. Cl.
CPC .......... *A61B 17/32002* (2013.01); *A61B 2017/00845* (2013.01); *A61B 2017/00946* (2013.01); *A61B 2017/320032* (2013.01)

(58) Field of Classification Search
CPC .......... A61B 17/32002; A61B 2017/00845; A61B 2017/320032
USPC ................. 606/170, 169, 180, 167
See application file for complete search history.

(56) References Cited

U.S. PATENT DOCUMENTS

| | | | | |
|---|---|---|---|---|
| 4,660,267 A * | 4/1987 | Wheeler | .......... | A61B 17/32002 29/437 |
| 5,665,101 A * | 9/1997 | Becker | ............ | A61B 17/32002 606/167 |
| 5,961,532 A * | 10/1999 | Finley | .............. | A61B 17/32002 604/22 |
| 8,475,482 B2 * | 7/2013 | Palmer | ................ | A61M 1/0023 606/170 |

* cited by examiner

*Primary Examiner* — Vy Bui
(74) *Attorney, Agent, or Firm* — Chalin A. Smith; Smith Patent, LLC

(57) ABSTRACT

Minimally invasive endoscopic cutting instruments having improved efficiency, access and reduced manufacturing costs are described herein. In particular, the present invention describes means for eliminating or modifying the distal end axial bearing surfaces so as to reduce manufacturing costs as well as the opportunity for galling and metal shedding. The present invention further describes an improved hub attachment method that may further or alternatively reduce overall manufacturing costs. The present invention yet further describes means and methods for improved bendability in the field, which, in turn, enables improved access to remote surgical targets.

15 Claims, 32 Drawing Sheets

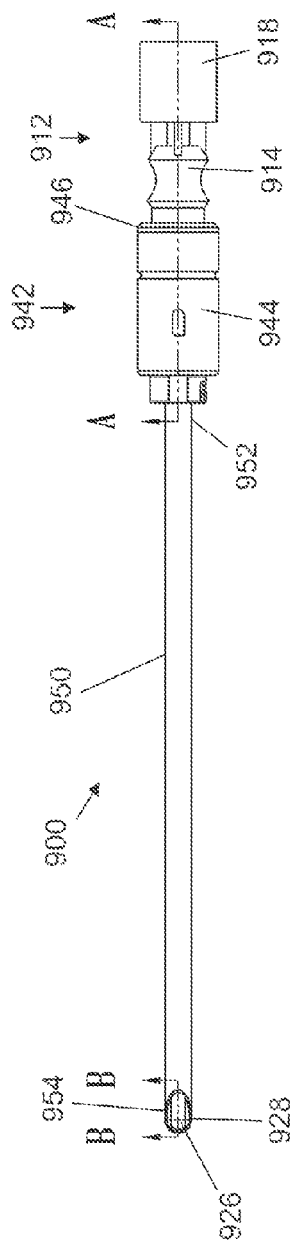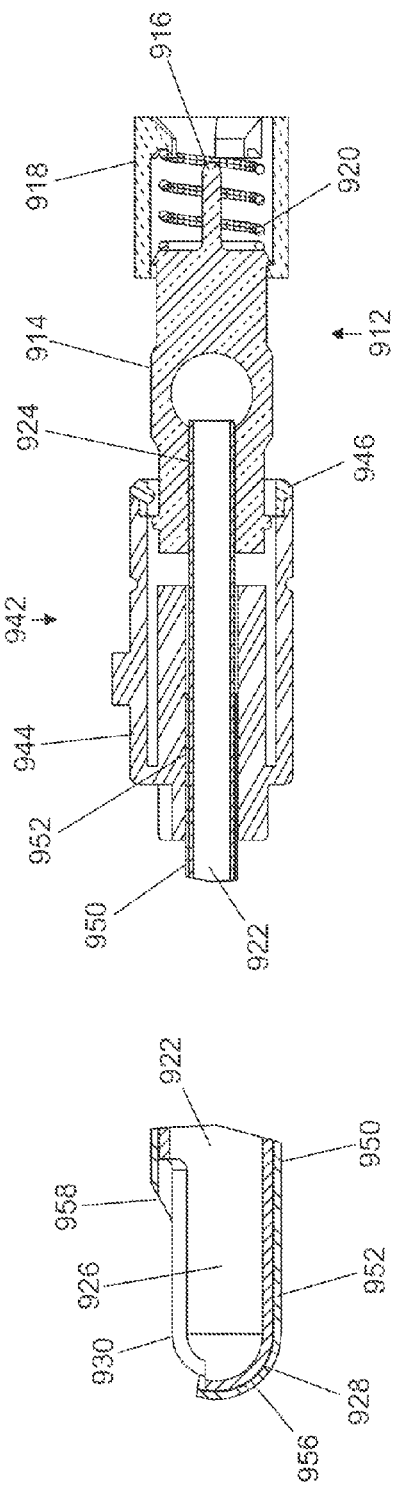
PRIOR ART
Fig. 1D
PRIOR ART
Fig. 1E
PRIOR ART
Fig. 1F

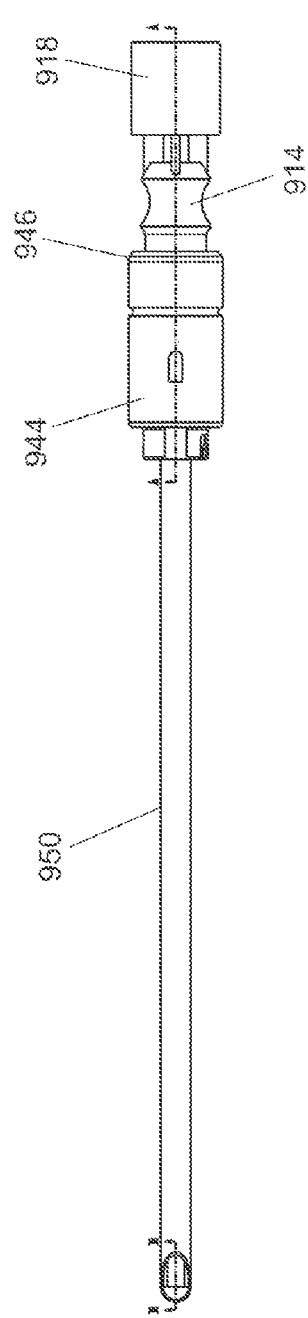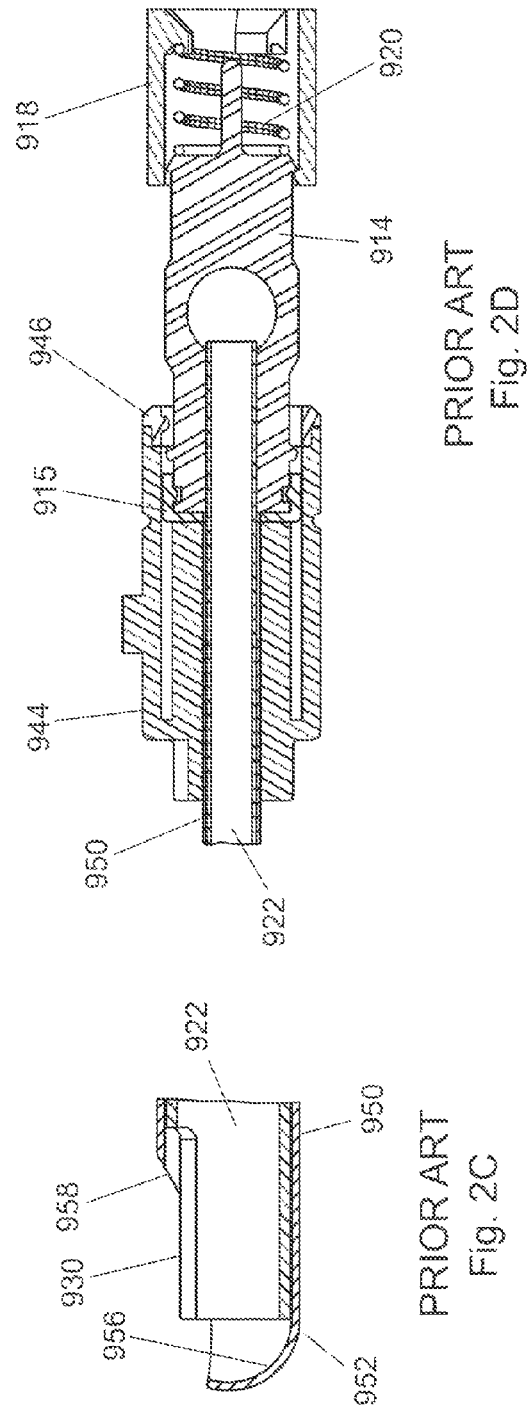
PRIOR ART
Fig. 2B
PRIOR ART
Fig. 2C
PRIOR ART
Fig. 2D

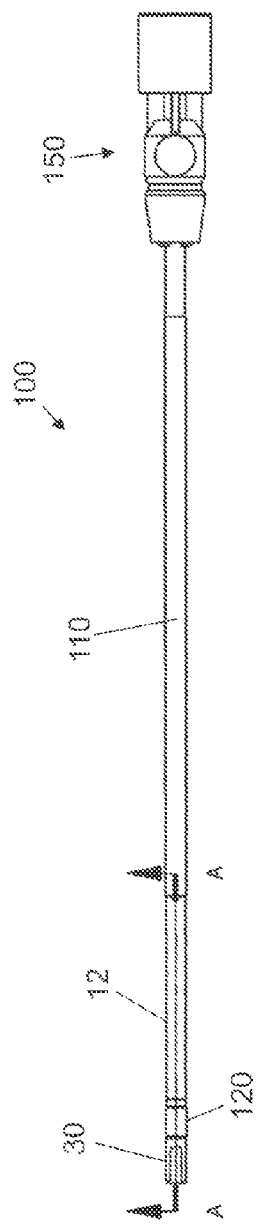
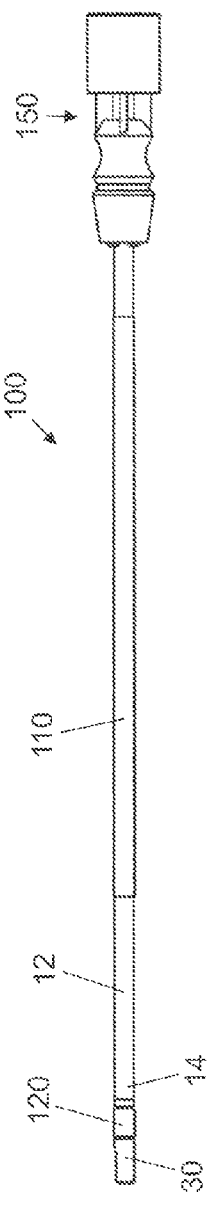
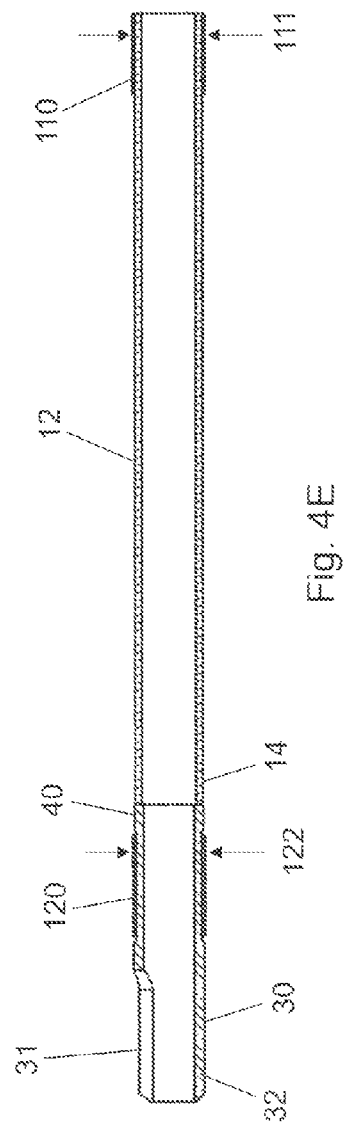
Fig. 4C
Fig. 4D
Fig. 4E

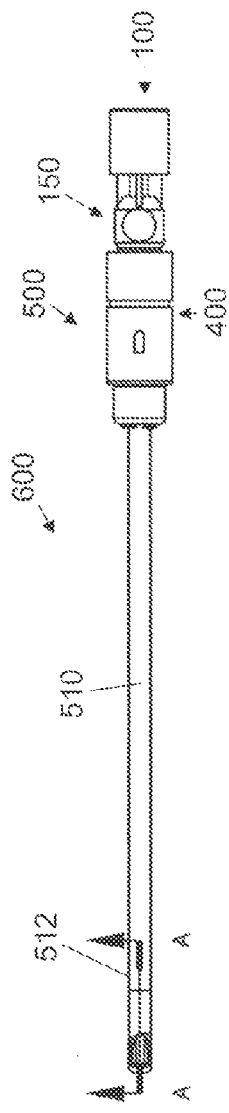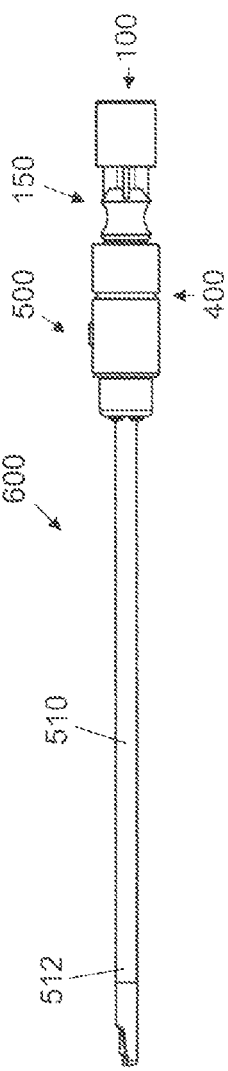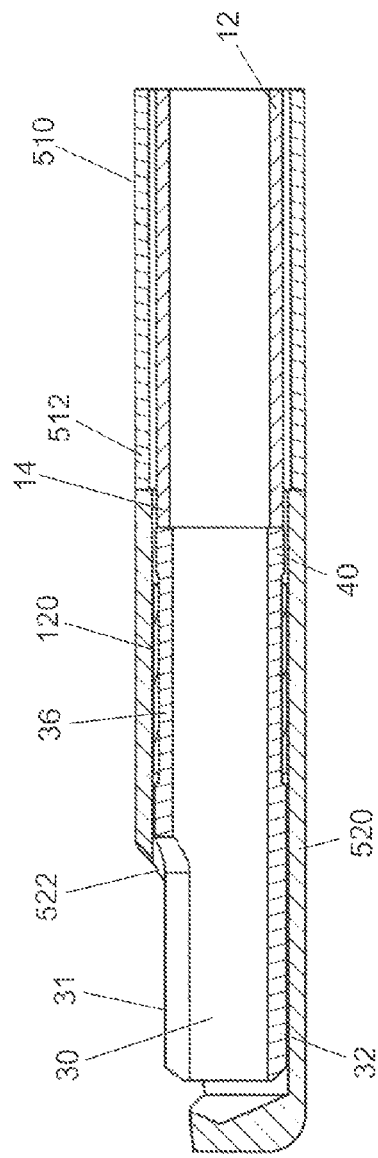
Fig. 6C
Fig. 6D
Fig. 6E

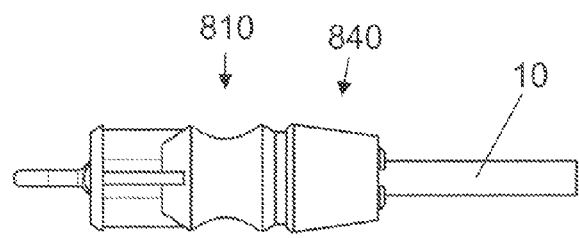
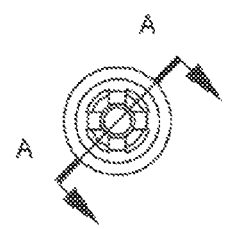
Fig. 17          Fig. 18
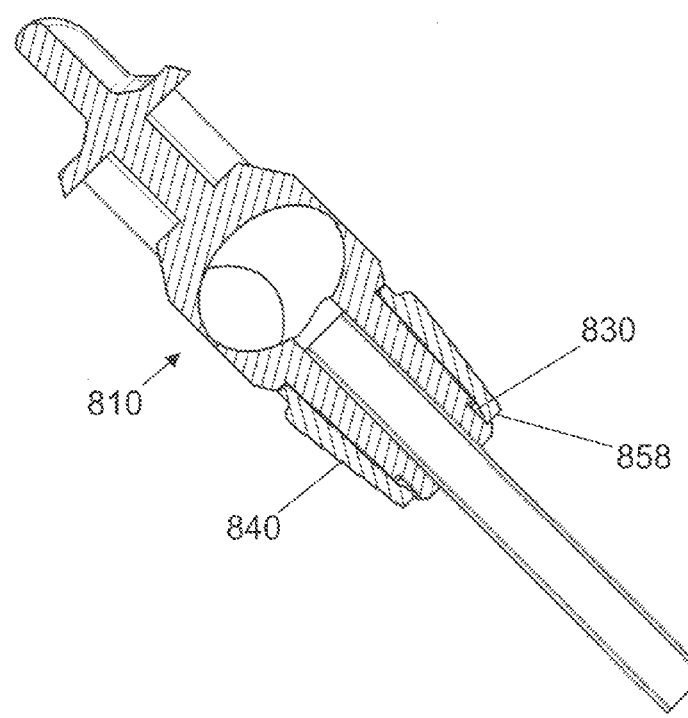
Fig. 19

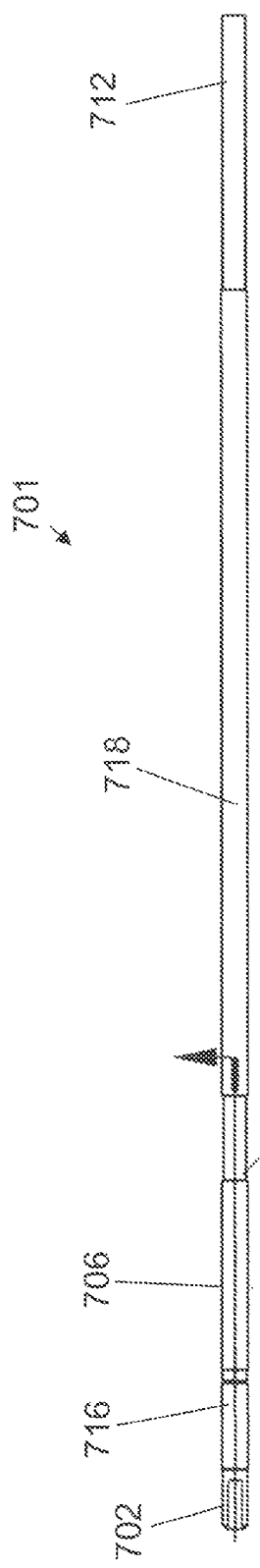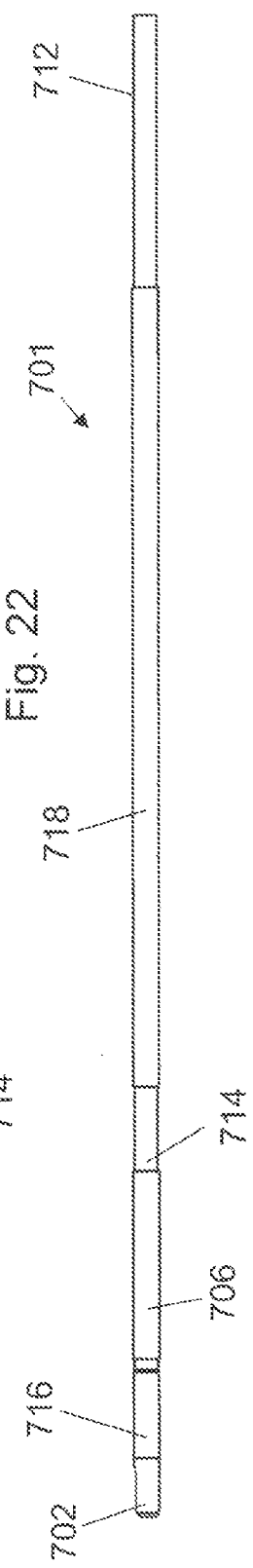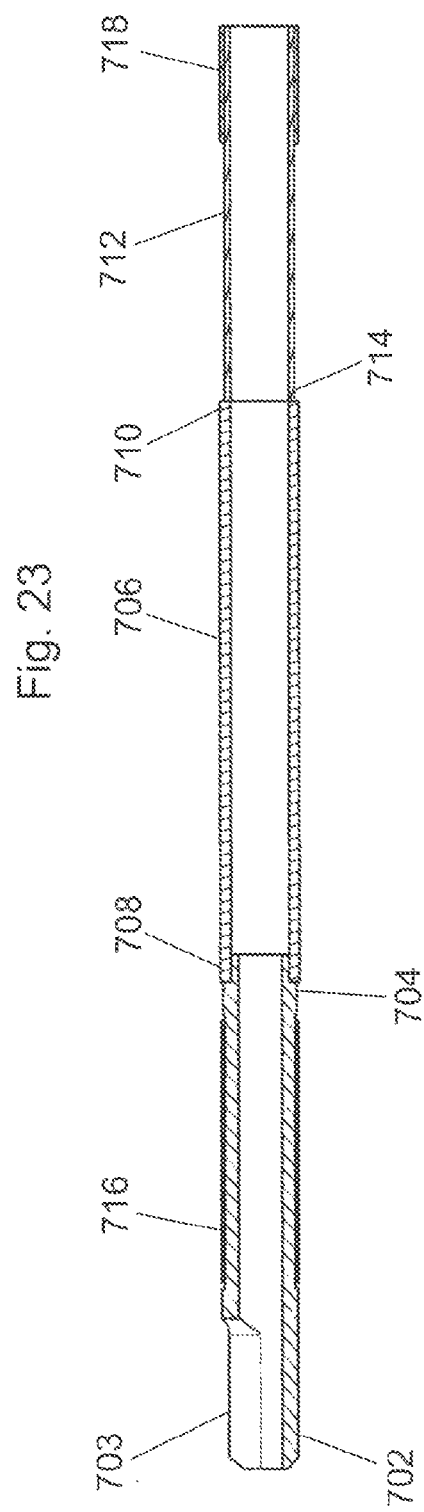

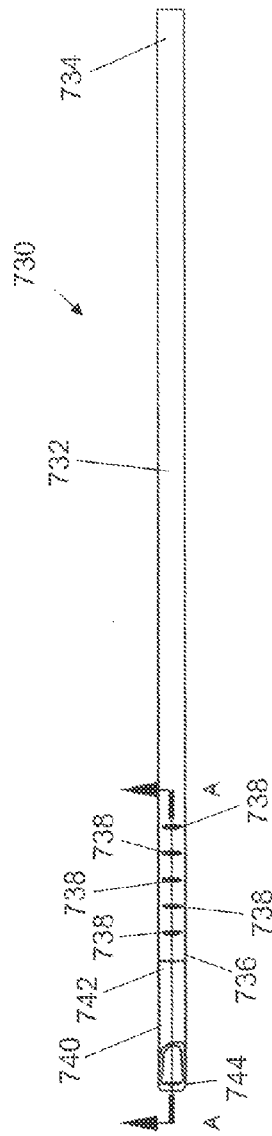
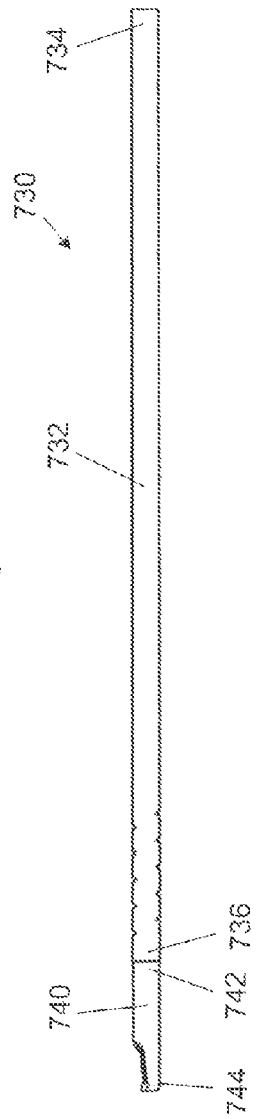
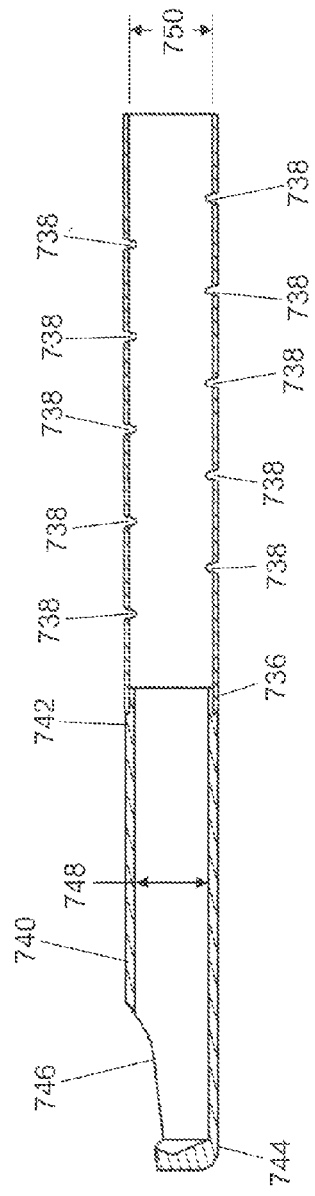
Fig. 27
Fig. 28
Fig. 29

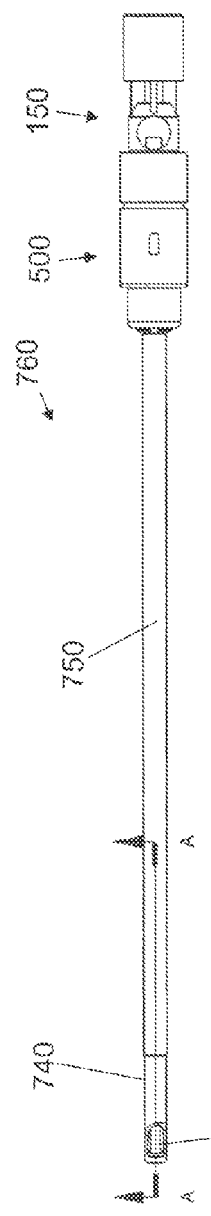
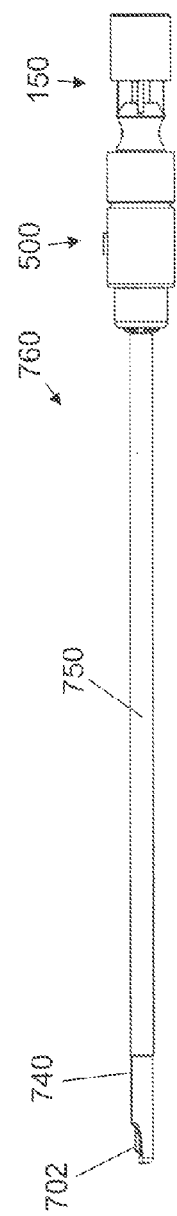
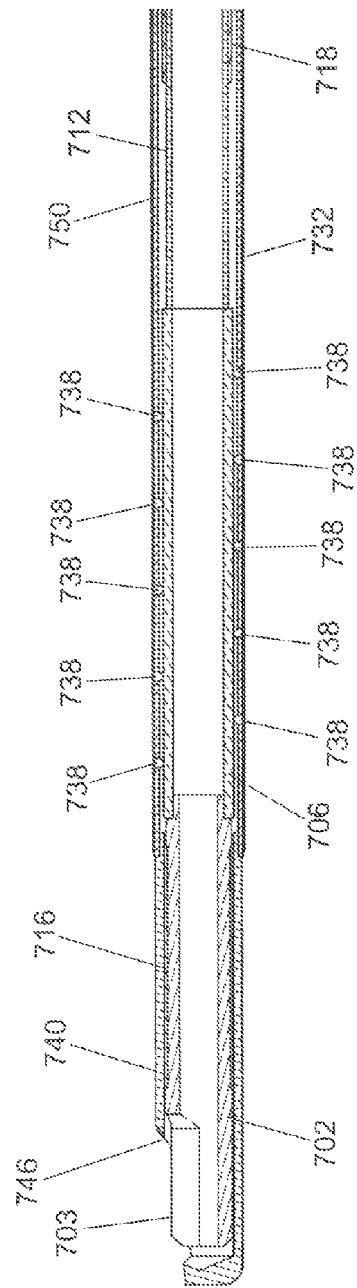
Fig. 30
Fig. 31
Fig. 32

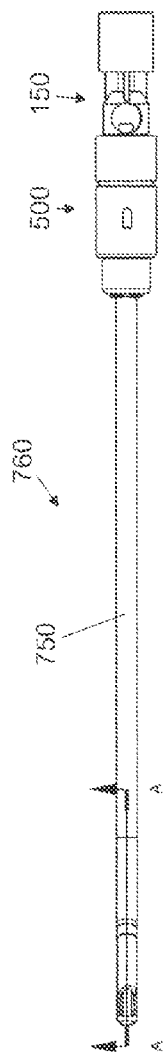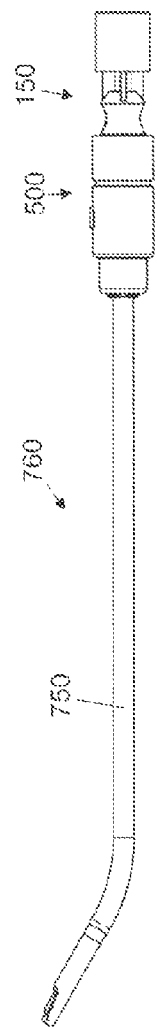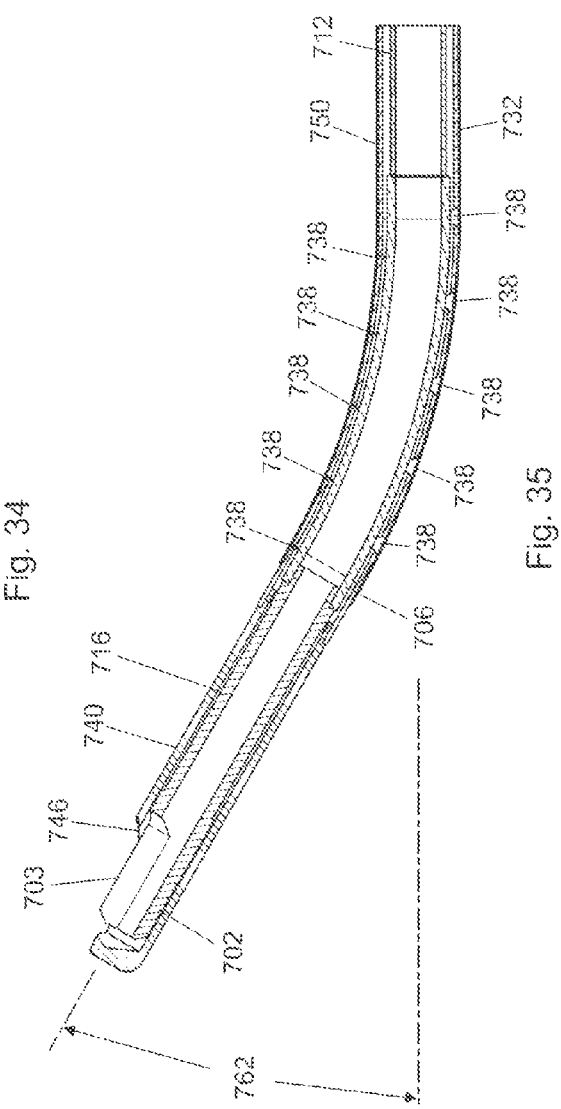
Fig. 33
Fig. 34
Fig. 35

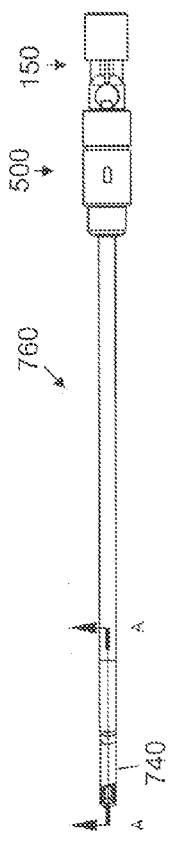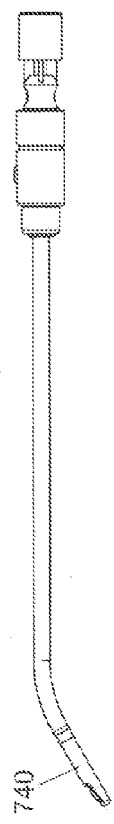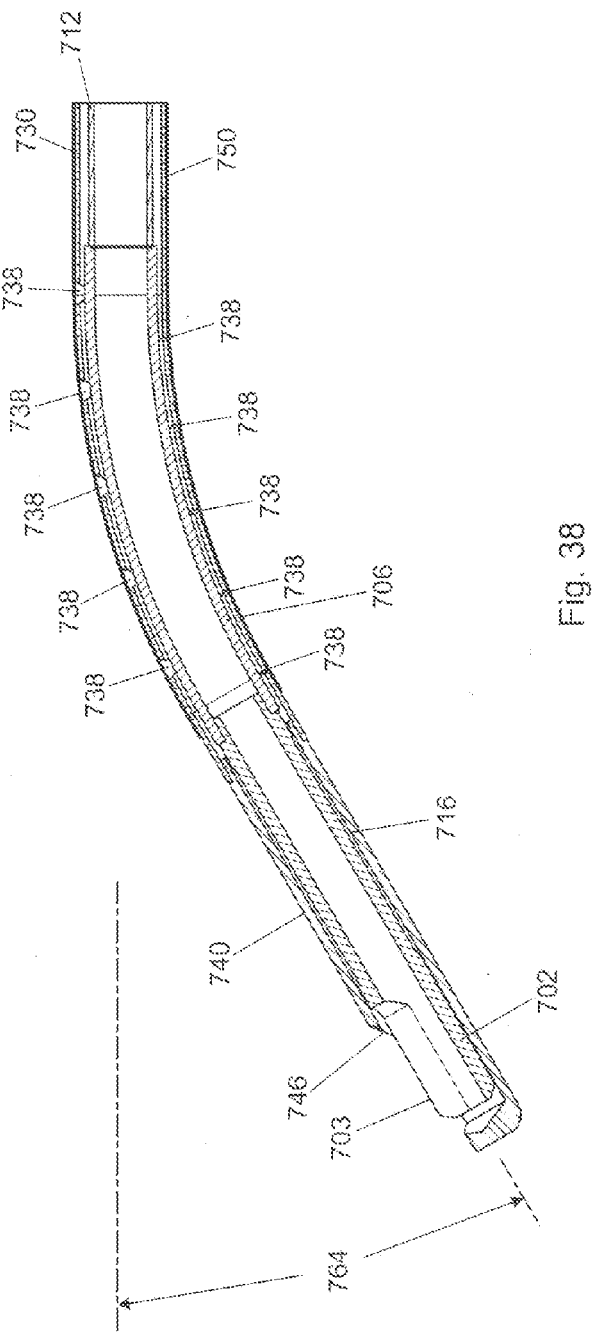
Fig. 36
Fig. 37
Fig. 38

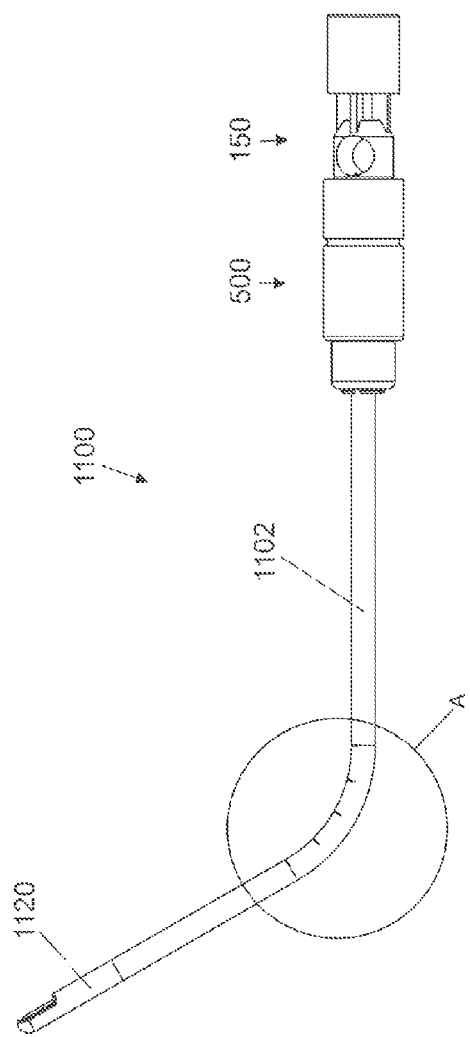
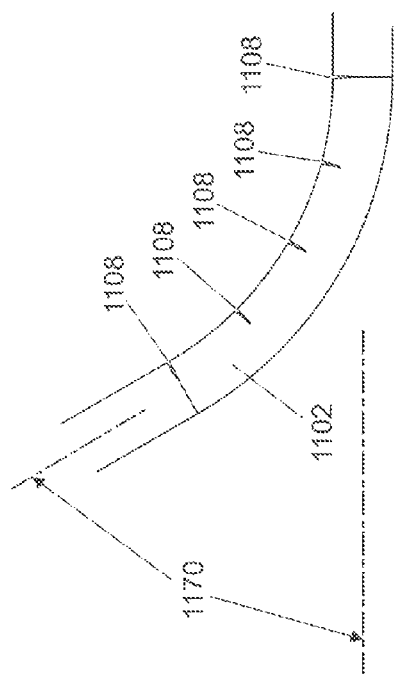

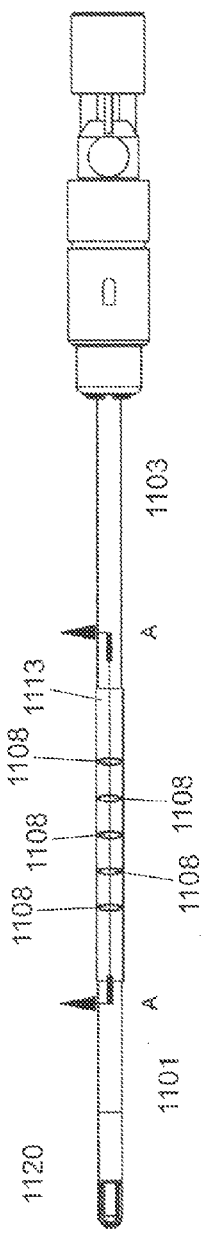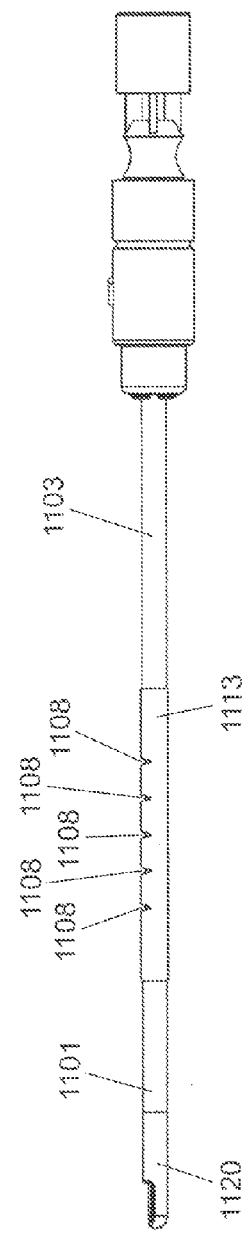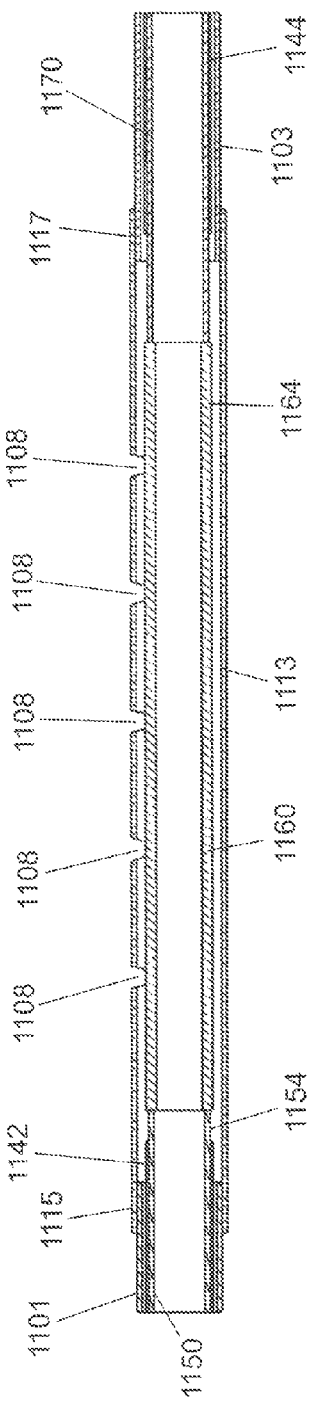
Fig. 48
Fig. 49
Fig. 50

ENDOSCOPIC CUTTING INSTRUMENTS HAVING IMPROVED EFFICIENCY AND REDUCED MANUFACTURING COSTS

PRIORITY

This application claims the benefit of U.S. Provisional Application Nos. 61/852,956 and 61/958,750 filed Mar. 25, 2013 and Aug. 5, 2013, respectively. The entire contents of these priority applications are incorporated by reference herein.

FIELD OF THE INVENTION

The present invention relates generally to field of endoscopy and more specifically to the elongated, powered surgical instruments that find use in the context of endoscopic tissue resection. More particularly, the invention relates to an endoscopic cutting instrument having an elongated inner tube rotatably situated within an elongated stationary outer tube, wherein both inner and outer tubes have, at their distal ends, cutting apertures that cooperate to resect tissue during endoscopic surgical procedures. Still more particularly, the invention relates to methods for improving the efficiency and reducing the manufacturing cost of such devices through the use of unique bearing and assembly construction and methods.

BACKGROUND OF THE INVENTION

In contrast to conventional surgery, which requires a relatively large incision in order to gain access to a surgical site within a body, endoscopic procedures utilize natural passages, or, alternatively, involve the formation of very small portals to gain access to the surgical site of interest. Accordingly, an endoscopic procedure is often referred to as "minimally invasive" or "closed" surgery. One advantage of performing a procedure endoscopically is that since the portions of the body that are cut are reduced, the portions of the body that need to heal after the surgery are likewise reduced. Still another advantage of endoscopic surgery is that it exposes less of the interior tissue of the body to the open environment. This minimal opening of the body lessens the extent to which its internal tissue and organs are open to infection.

Advancements in this field of "closed" surgery, such as arthroscopy and, more generally, endoscopic surgery, have led to the creation of numerous minimally invasive surgical cutting instruments. As noted above, in closed surgery, access to the surgical site is gained via one or more portals. As such, the instruments used in the surgical procedure must be sufficiently flexible, smooth and elongated to permit the distal ends of the instruments to reach the surgical site with minimal trauma to neighboring tissues. One end of the instrument, often referred to as the "distal end", is designed to be positioned at the surgical site. The opposed end of the instrument, often referred to as the "proximal end", extends out of the patient's body. The distal end of the instrument is typically provided with some type of working head designed to manipulate the tissue against which it is placed whereas the proximal end of the instrument is provided with a mechanism for the user to remotely control the working head.

Surgical cutting instruments for use in closed surgery—often referred as endoscopic "shavers"—are typically composed of a pair of concentrically disposed, close-ended, generally tubular members, more typically an elongated outer tubular member terminating in a distal opening or "cutting window", i.e., an aperture situated in the distal region, on the distal end or side wall, or both, and an elongated inner tubular member, slidably and concentrically disposed in the outer tubular member, whose distal end is disposed adjacent the cutting window of the outer tubular member. The distal end of the inner tubular member typically has a surface or edge for engaging tissue via the distal opening in the outer tubular member and cooperates with the opening to shear, cut or trim tissue, a process often referred to as "resection". For example, the inner tubular member may be rotatably driven about its axis from its proximal end by a handpiece having a small electric motor which is controlled by one or more finger actuated switches on the handpiece, one or more foot switches on a console supplying power to the handpiece, or some other analogous control means. Cut tissue can then be aspirated through the hollow lumen of the inner tubular member to be collected via a vacuum tube communicating with the handpiece. The distal end of the inner tubular member can be provided with a number of dimensions or configurations, depending upon the surgical procedure to be performed. Similarly, the opening in the distal end of the outer tubular member may be adapted to cooperate with the particular configuration of the distal end of the inner tubular member. For example, the inner and outer tubular members can be configured to produce side cutting or end cutting, or a combination of the two, to cut soft or bony tissues or combinations thereof. These various configurations are generally referred to in the art as "shaver blades".

Coordinating inner and outer cutting windows of a shaver each have perimeters that are generally composed of two relatively longitudinal, straight or curvilinear edges connected at their proximal ends and distal ends by two relatively transverse edges. The configuration of the longitudinal edges, and to a lesser extent the transverse edges is determined by the intended use of the shaver. For instance, shavers intended for use on soft tissue will be provided with cutting windows configured for increased resection efficiency but relatively low resistance to deformation since the cutting forces are typically low. Conversely, those shavers intended for use on tough tissue, such as meniscus or vertebral discs, will be provided with a greater resistance to deformation since the cutting forces are quite high.

The inner and outer tubular members are generally metallic and typically have at their proximal ends plastic hubs mounted thereto. The proximal ends of the metallic tubular members are typically knurled (i.e., manufactured, typically via a lathe, to include diamond-shaped or criss-cross pattern that is cut or rolled into metal). The tube and hub components are assembled together by heating them with an induction heater and then forcing the tubular component into the lumen of the hub such that the plastic is melted and bonds to the knurled portion of the tube. While this bonding method is in common use, it has drawbacks in that it requires an induction heater and complex affixture for aligning the distal end of the tubular member with the lumen of the hub, and for ensuring that the hub is properly positioned axially on the tube. The axial (or longitudinal) position is particularly important since skewed alignment and/or improper positioning may make the shaver inoperable.

As noted above, resection of tissue by a shaver blade is typically accomplished by cooperative interaction between the edges of the inner and outer cutting windows. As the inner and outer windows come into alignment, vacuum within the lumen of the inner tube sucks tissue into the opening formed. Continued rotation of the inner member causes the inner cutting edges to approach the outer cutting edges. Tissue in the cutting window between the inner and outer edges is either trapped between the edges or ejected from the window. Tissue trapped between the edges is either cut by the edges as they approach each other or torn by the cutting edges as they pass and rotate away from each other. The resected tissue is aspirated from the site through the inner lumen of the inner tube.

To produce an efficient cutting action, the clearance between the inner and outer tubular members is necessarily quite small, generally on the order of 0.2 mm (0.008 inches) or less as excessive clearance can result in tearing rather than cutting of tissue. However, lateral forces caused by cutting of tissue, particularly dense fibrous tissue like meniscus, may cause deflection of the inner tubular member within the outer tubular member so as to allow contact between the inner and outer cutting edges. This contact causes the cutting edges to dull, and more importantly, may generate metallic debris that is then deposited into the surgical site, with negative consequences to the patient. Metallic debris may also be created through rubbing contact between the distal portions of the inner and outer tubes in close proximity to the cutting windows during high-speed operation. Such rubbing may cause galling and cold-welding of the elongate metallic members in the regions in contact. In severe cases, galling may cause welding of the inner and outer members so as to make the shaver unusable.

To prevent such dulling, galling and welding, materials of the inner and outer distal ends are carefully selected and the components hardened and machined to very precise shapes, frequently with form tolerances of as little 0.0002 inches. The surface finishes of the bearing surfaces are also critical since irregularities in the surfaces can lead to high-localized stresses which, in turn, can result in galling of the surfaces during use. To address this issue, some manufacturers coat the inner member bearing surface with a gall-resistant metallic material, while others make the distal end of the inner member from a gall resistant alloy. In any event, galling and metallic debris created by shaver blades is still a frequent problem since inspection of the inner surface of the outer member is very difficult and minor manufacturing abnormalities can create surfaces which are not to specification. Because of these and other factors, forming of the inner and outer distal end bearing surfaces is a significant portion of the shaver blade manufacturing costs.

Another art-recognized manufacturing hurdle involves shaping and bending of the distal portion of the device. Access to certain structures during endoscopic surgery of knees, shoulders or other joints may occasionally be difficult, particularly when using a standard shaver blade. Because of this, endoscopic shavers are often configured with a distal portion that is angularly offset from the axis of the shaver handpiece and proximal portion. With shaver blades and burs having an angularly offset distal portion, surgeons can access portions of the anatomy not readily reached with standard unbent shavers. The distal portions of these devices are usually formed to the desired angular offset during manufacture, with typical offsets being on the order of twenty degrees or less. Bending fixtures and dies are used to produce repeatable bends with small radii. Other powered endoscopic devices, like the Merlin line of shaver blades available through Conmed (Utica, N.Y.), are supplied to the surgeon without an angular offset but allow the surgeon to bend the device to the desired offset in the operating room with the aid of an included bending device capable of producing a large bend radius that is distributed along the distal outer tube.

Critically, devices are generally supplied as either prebent or bendable in the field, but not both (i.e., pre-bent devices that are then further bendable in the field). The elongate tubular sections used for the distal portions of endoscopic shavers and burrs have uniform structural properties throughout their length. Bending of the tubular section during manufacture allows the use of dies and other tooling that are able to repeatably produce bends having a small radius. Attempting to modify the angular offset of such a pre-bent blade would be expected to result not in modification of the original bend, but in bending at locations on the tubular member adjacent to the bend produced during manufacture. Bending of the tube during manufacture work-hardens the material in the bent region so that any attempt to modify the bend will cause adjacent regions which have not been work-hardened to deform. For the same reason, bendable products like the Conmed Merlin shaver blade are formed with large bend radii so that significant work-hardening of the tubing does not occur. These bendable devices can be bent to an initial angular offset and then to another offset; however, the large bend radii severely limits the utility of these bendable devices. To access most structures, it is necessary that the bend have a small radius and be positioned near the distal end of the shaver blade.

SUMMARY OF THE INVENTION

Despite the afore-noted improvements in the art, there remains a clear need in the art to increase the efficiency and access of endoscopic cutting instruments and shaver blades and to reduce their manufacturing costs. The present invention is directed to these needs. In particular, it is a primary goal of the present invention to reduce manufacturing costs through the elimination of and/or modification to the distal end axial bearing. As discussed in detail herein, manufacturing costs may be alternatively or further reduced through the use of an improved hub configuration that is a subject of the present invention.

It is a further goal of the present invention to provide an endoscopic shaver device with a reduced opportunity for galling and metal shedding by eliminating or modifying the distal end axial bearing. To that end, the present invention facilitates shaver manufacture through the elimination of critical distal bearing surface features which, under conventional practices, must be formed to close tolerances and which are difficult to inspect.

It is yet another goal of the present invention to provide for the manufacture of optimally bendable and re-bendable endoscopic shavers, more particularly pre-bent devices that are then further bendable in the field as needed.

In the context of the present invention, an endoscopic cutting instrument is characterized by an elongated inner member axially slidably and rotatably situated within an elongated stationary outer member, wherein both inner and outer members have at their distal ends cutting apertures which cooperate to resect tissue during endoscopic surgical procedures. As noted above, prior art shavers with tubular inner and outer distal assemblies maintain axial positioning between the assemblies by applying a distal force to the inner assembly so that the closed distal end of the inner member maintains makes contact with the distal inner surface of the outer assembly. The two surfaces together form a distal bearing, with the distal force being supplied by a compression spring, either as a part of the shaver assembly or the handpiece into which the shaver is removably mounted. Contact stresses (Hertzian in the case of spherical surfaces) at the distal bearing surfaces can be high and can cause galling and generation of metallic debris if the surfaces are improperly designed or formed. It is thus a primary goal of the instant invention to eliminate this distal bearing, or provide means for making the contact at the distal bearing intermittent so that surfaces do not undergo high localized heating and galling. Accordingly, it is first objective of the present invention to provide a shaver blade with a unique bearing system that prevents contact between the inner and outer distal portions of the tubular members.

In accordance with this objective, the present invention provides an endoscopic shaver device having concentric inner and outer tubular members each having an aperture formed in its distal for the cooperative cutting of tissue introduced thereto by a vacuum applied to the lumen of the inner tubular member. The inner tubular member has at its distal end a portion having a first diameter, and the remainder of the tube proximal thereto having a second smaller diameter. The first, distal portion of the inner tubular member has formed at its distal end an aperture forming a cutting window, and proximal thereto a recessed portion wherein is positioned a polymeric tubular member or sleeve having an outer diameter greater than the first diameter of the distal portion. When positioned within the outer tubular member, the polymeric sleeve acts as a bearing so as to prevent contact between the distal portion of the inner member and the lumen of the outer tubular distal portion.

In a preferred embodiment, the distal portion and proximal portion of the inner tubular member comprise discrete elements that are joined by welding, brazing or another joining process. The elements may be of the same alloy or may alternatively be dissimilar. In yet another preferred embodiment, the outer tubular member is provided with a distal portion having a first inside diameter, and a proximal remainder having a second larger diameter, wherein the length of the distal portion is such that the polymeric bearing on the inner distal portion is positioned within the outer tubular member distal portion. In another preferred embodiment, the distal portion and the proximal remainder of the outer member are discrete elements joined by welding, brazing or another joining method. In some embodiments, the discrete distal portion and discrete proximal portion are made of the same alloy. In others they are dissimilar.

Other shavers have been constructed using polymeric bearings on the inner tubular member. However, all previous shavers have positioned the bearing on the reduced diameter proximal portion. This has two effects. Because the bearing is displaced axially from the proximal end of the cutting window, flexing of the inner tubular member may still allow contact between the inner and outer cutting edges, or may allow rubbing between the outer surface of the inner tubular member and the inner surface of the outer member in the distal region adjacent to the cutting windows. Also, the method used to decrease the diameter of the proximal portion of the inner tubular member is frequently centerless grinding, a process in which concentricity between the distal and reduced proximal portion is not guaranteed. Eccentricity between these portions, when the bearing is on the reduced portion, may cause rubbing between the distal surfaces of the inner and outer tubular members, an undesirable condition that may lead to galling and the generation of metallic debris. For these reasons, the presently available options are not ideal and thus the present invention represents a marked improvement thereover.

A second objective of the present invention is to provide an endoscopic shaver device that may be inexpensively produced through an improved low-cost method for mounting the hubs to the proximal end of the elongate tubular members More particularly, the endoscopic shaver of the present invention may use a unique method for joining the inner hub to the inner tubular member, and for joining the outer hub to the outer tubular member. In each case, the hub has a conically tapered distal portion having axially extending slots formed therein that allow for slight radially inward deflection when a force is applied thereto. In a preferred embodiment, the tubular member is made of metal, the proximal end of the member is knurled, and the knurled portion inserted into the lumen of the hub, wherein at least a portion of the knurled portion is positioned within the slotted conical distal portion of the hub. A polymeric collar having a conical inner surface complementary to that of the conical hub distal portion is then positioned on the distal hub portion so as to compress the hub portion inward in a manner that causes the knurled portion of the tubular element to be gripped tightly within the hub lumen. The collar is then pressed axially onto the hub distal portion. In this manner, the present invention may avoid the unduly complicated and costly manufacturing procedures required by the prior art.

A third objective of the present invention to provide endoscopic shavers with a distal portion that may be angularly offset by the surgeon during use by bending of the outer tubular member at a predetermined axial location, wherein the initial bend is produced during manufacture of the device, or by the surgeon at time of use. Unlike the bent and bendable devices of the prior art, endoscopic shavers of the instant invention may be rebent to other angles during use, the bend remaining in the predetermined axial location. Unlike other bendable endoscopic shaver blades, the distal portion of the blade may be bent in a first direction so that the cutting window is on the concave size of the bend, and then rebent so that it is on the convex side, or vice versa. In other embodiments, while the blade distal portion is bendable and rebendable, the cutting window remains on the concave side of the bend or on the convex side of the bend, with the degree of angular offset of the distal portion being modifiable.

Rebendable shavers of the instant invention include a distal tubular member having non-uniform flexular strength throughout its length. Specifically, a portion of the tubular member near its distal end has its flexular strength reduced such that an initial small-radius bend and angular offset may be produced in the tubular member during manufacture or by the surgeon at time of use, and the surgeon can modify the angular offset in the operating room to suit specific anatomy through the use of a manual bending device. The angular offset of the distal end of the tubular member may be modified by modifying the degree of bend. However the deformation of the member remains localized in the bend region since adjacent portions of the tubular member have a higher flexular strength. Illustrative mechanisms for altering and/or reducing the flexular strength in the bend region contemplated by the present invention include, but are not limited to (i) notching the tube in the bend region, (ii) annealing the tube in the bend region, (iii) reducing the wall thickness in the bend region, and any combination thereof.

It will be understood by those skilled in the art that one or more aspects of the present invention can meet certain of the afore-noted objectives, while one or more other aspects can meet certain other objectives. Each objective may not apply equally, in all its respects, to every aspect of this invention. As such, the preceding and any subsequently presented objectives can be viewed in the alternative with respect to any one aspect of this invention.

These and other objectives are accomplished in the invention herein described, directed to an endoscopic shaver blade having improved efficiency and reduced manufacturing costs. Further objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not constructed as limiting of the invention.

BRIEF DESCRIPTION OF THE DRAWINGS

Various aspects and applications of the present invention will become apparent to the skilled artisan upon consideration of the brief description of figures and the detailed description of the present invention and its preferred embodiments that follows:

FIGS. 1A to 1F depict various views of a prior art endoscopic shaver device. In particular, FIG. 1A depicts a perspective view of an exploded assembly for a prior art endoscopic shaver. FIG. 1B is a side elevational view of an outer assembly for the prior art shaver of FIG. 1A. FIG. 1C is a side elevational view of an inner assembly for the prior art shaver of FIG. 1A. FIG. 1D is a plan view of the prior art shaver of FIG. 1A. FIG. 1E is an expanded sectional view of the objects of FIG. 1D at location B-B. FIG. 1F is an expanded sectional view of the objects of FIG. 1D at location A-A.

FIGS. 2A to 2D depict various views of a second prior art endoscopic shaver. In particular, FIG. 2A depicts a perspective view of an exploded assembly for a prior art endoscopic shaver embodying the principles of Heisler in U.S. Pat. No. 8,313,502. FIG. 2B is a plan view of the assembled shaver of FIG. 2A. FIG. 2C is an expanded sectional view of the objects of FIG. 2B at location B-B. FIG. 2D is an expanded sectional view of the objects of FIG. 2B at location A-A.

FIG. 3A is a perspective view of the distal elements of an inner assembly for an endoscopic shaver formed in accordance with the principles of this invention. FIG. 3B is an expanded view of the objects of FIG. 3A at location A. FIG. 3C is a plan view of the objects of FIG. 3A. FIG. 3D is a side elevational view of the objects of FIG. 3A. FIG. 3E is a side elevational sectional view of the objects of FIG. 3C at location A-A.

FIGS. 4A to 4E depict various views a further embodiment of an inner tubular assembly of an endoscopic shaver formed in accordance with the present invention. In particular, FIG. 4A is a perspective view of an inner assembly for an endoscopic shaver formed in accordance with the principles of this invention. FIG. 4B is an expanded view of the objects of FIG. 4A at location A. FIG. 4C is a plan view of the objects of FIG. 4A. FIG. 4D is a side elevational view of the objects of FIG. 4A FIG. 4E is an expanded sectional view of the objects of FIG. 4A at location A-A of FIG. 4C.

FIG. 5A is a perspective view of an outer assembly for an endoscopic shaver formed in accordance with the principles of the instant invention. FIG. 5B is an expanded perspective view of the objects of FIG. 5A at location A. FIG. 5C is a plan view of the objects of FIG. 5A. FIG. 5D is a side elevational view of the objects of FIG. 5A. FIG. 5E is an expanded sectional view of the objects of FIG. 5A at location A-A of FIG. 5C.

FIGS. 6A to 6E depict various views the inner and outer tubular assemblies of FIGS. 4 and 5, respectively, assembled together in accordance with the present invention. In particular, FIG. 6A is a perspective view of an endoscopic shaver of the instant invention. FIG. 6B is an expanded view of the distal portion of the objects of FIG. 6A at location A. FIG. 6C is a plan view of the objects of FIG. 6A. FIG. 6D is a side elevational view of the objects of FIG. 6A. FIG. 6E is an expanded sectional view of the objects of FIG. 6A at location A-A of FIG. 6C.

FIG. 17 is a side elevational view of the objects of FIG. 16.

FIG. 18 is a distal axial view of the objects of FIG. 16.

FIG. 19 is a sectional view of the objects of FIG. 16 at location A-A of FIG. 18.

FIG. 22 is a plan view of the inner tubular assembly for an alternate embodiment rebendable shaver of the instant invention.

FIG. 23 is a side elevational view of the objects of FIG. 22.

FIG. 24 is an expanded sectional view of the distal portion of the objects of FIG. 22 at location A-A.

FIG. 27 is a plan view of the objects of FIG. 25.

FIG. 28 is a side elevational view of the objects of FIG. 25.

FIG. 29 is an expanded sectional view of the distal portion of the objects of FIG. 27 at location A-A.

FIGS. 30 to 38 depict various views of the inner and outer tubular assemblies of FIGS. 22 and 25, respectively, assembled together in accordance with the present invention. In particular, FIG. 30 is a plan view of the of a rebendable shaver embodiment of the instant invention in an initial unbent condition. FIG. 31 is a side elevational view of the objects of FIG. 30. FIG. 32 is an expanded sectional view of the objects of FIG. 30 at location A-A. FIG. 33 is a plan view of the of an alternate embodiment rebendable shaver of the instant invention having a distal portion bent to a first angle. FIG. 34 is a side elevational view of the objects of FIG. 33. FIG. 35 is an expanded sectional view of the objects of FIG. 33 at location A-A. FIG. 36 is a plan view of the of an alternate embodiment rebendable shaver of the instant invention having a distal portion bent to a second angle. FIG. 37 is a side elevational view of the objects of FIG. 36. FIG. 38 is an expanded sectional view of the objects of FIG. 36 at location A-A.

FIG. 44 side elevational view of the alternate embodiment shaver of FIG. 39 at the completion of manufacturing as supplied to the user having its distal portion angularly offset to a first angle.

FIG. 45 is an expanded view of the objects of FIG. 44 at location A.

FIG. 48 is a plan view of an alternate embodiment.

FIG. 49 is a side elevational view of the objects of FIG. 48.

FIG. 50 is an expanded sectional view of the objects of FIG. 49 at location A-A.

DESCRIPTION OF THE PREFERRED EMBODIMENTS

Figure 1A:
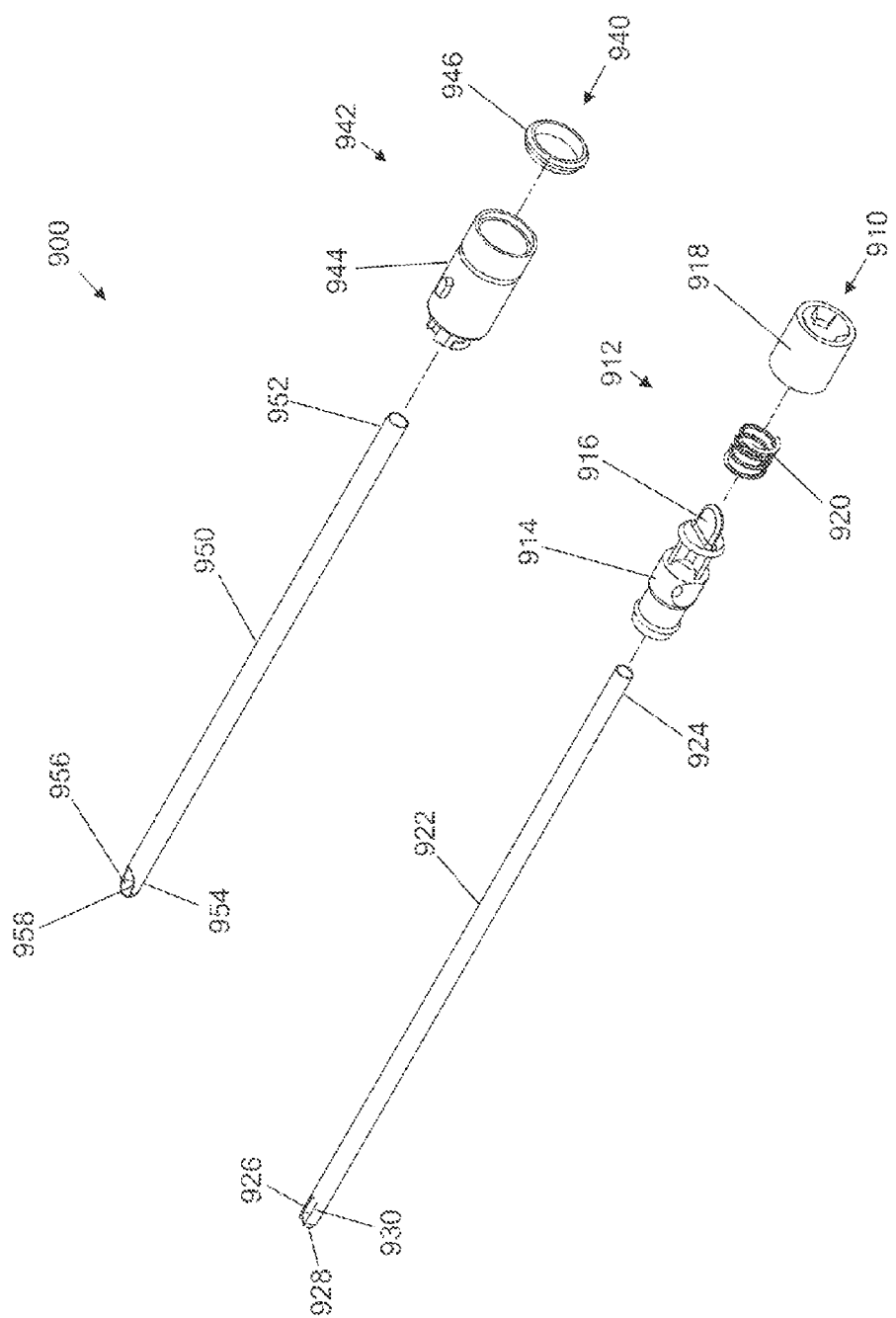
Figure 1B:
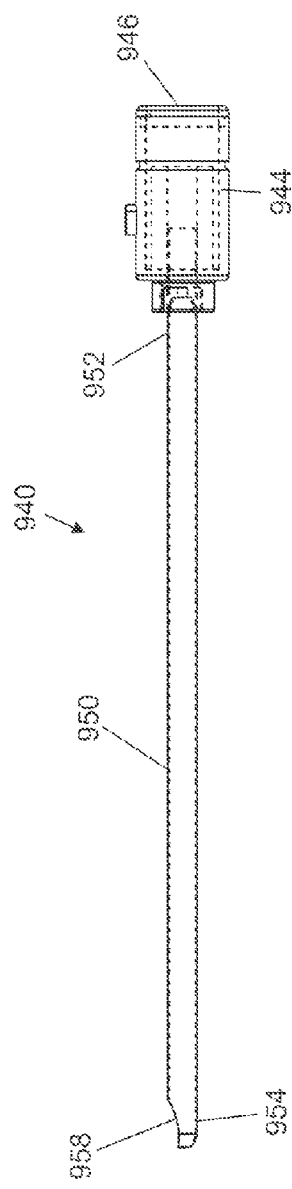
Figure 1C:
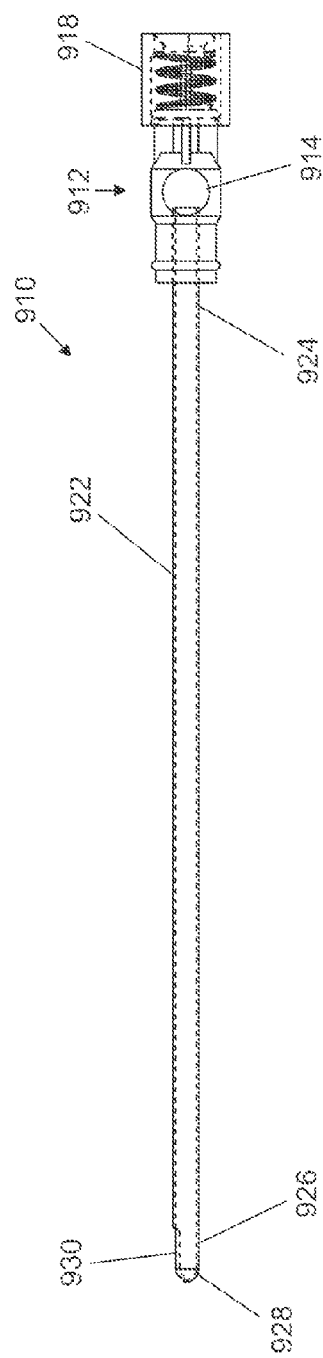
Figure 2A:
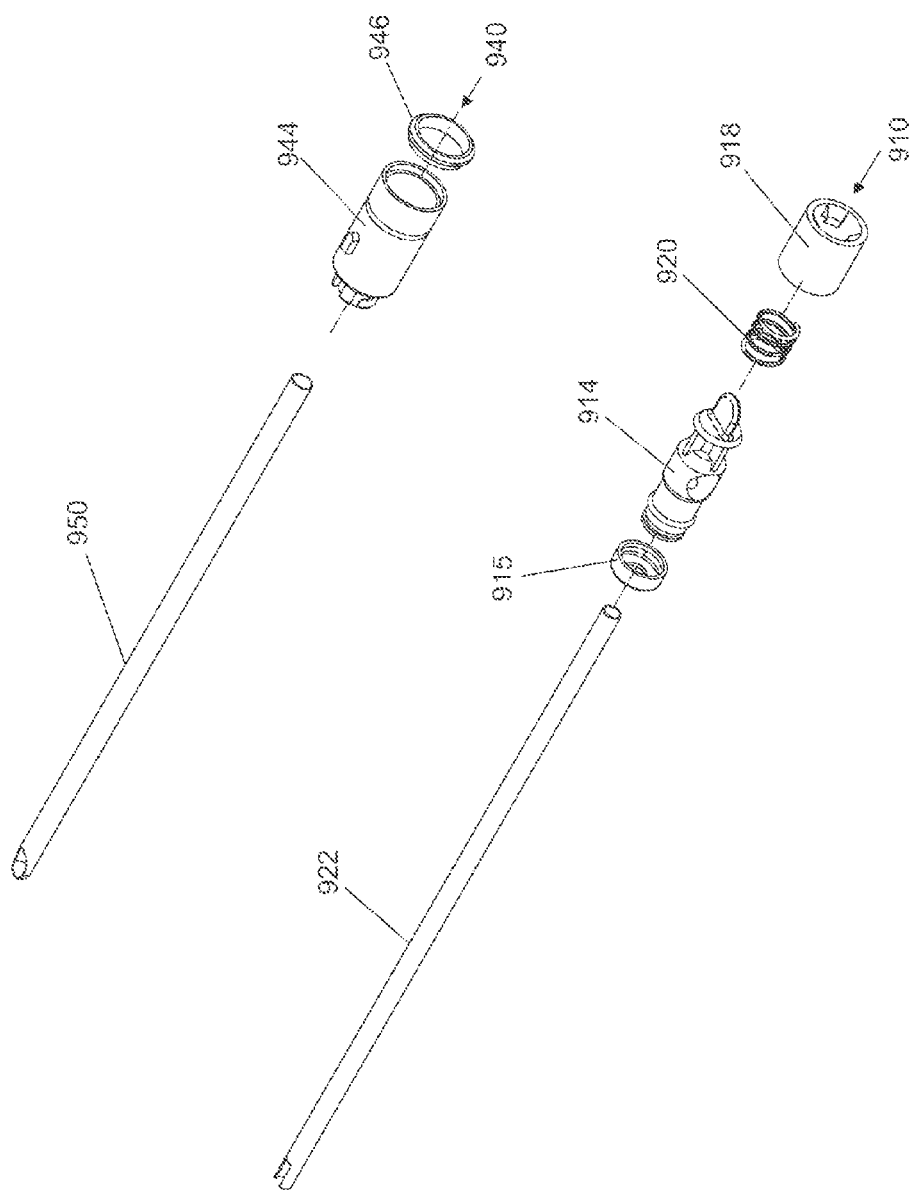

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Unless otherwise defined, all technical and scientific terms used herein have the same meaning as commonly understood by one of ordinary skill in the art to which the present invention belongs. However, in case of conflict, the present specification, including definitions, will control.

In the context of the present invention, the following definitions apply:

The words "a", "an" and "the" as used herein mean "at least one" unless otherwise specifically indicated. Thus, for example, reference to an "aperture" is a reference to one or more apertures and equivalents thereof known to those skilled in the art, and so forth.

The term "proximal" as used herein refers to that end or portion which is situated closest to the user of the device, farthest away from the target surgical site. In the context of the present invention, the proximal end of the inventive device includes the handpiece region.

The term "distal" as used herein refers to that end or portion situated farthest away from the user of the device, closest to the target surgical site. In the context of the present invention, the distal end of the inventive device includes the respective cutting windows of the inner and outer tubular members.

In the context of the present invention, the terms "shaver", "shaver blade", "endoscopic shaver" and "endoscopic cutter" are used interchangeably to refer to the family of elongate, powered surgical instruments used for endoscopic tissue resection.

The term "rotational" as used herein refers to the revolutionary movement about the center point or longitudinal axis of a device. In the context of the present invention, rotation of the elongated inner tubular member relative to the elongated outer tubular member of a conventional endoscopic shaver, which typically is held in a stationary position, results in relative rotation of their respective cutting apertures that coordinate to resect target tissue within the surgical site of interest.

The terms "lengthwise" and "axial" as used interchangeably herein to refer to the direction relating to or parallel with the longitudinal axis of a device. The term "transverse" as used herein refers to the direction lying or extending across or perpendicular to the longitudinal axis of a device. The term "lateral" pertains to the side and, as used herein, refers to motion, movement, or materials that are situated at, proceeding from, or directed to a side of a device.

The present invention makes reference to "bearings" and "bearing surfaces". The terms "bearing" and "bearing surface" refer to elements and surfaces that constrain relative motion between two parts, typically rotation or linear movement. Bearings may be classified broadly according to the motions they allow and according to their principle of operation as well as by the directions of applied loads they can handle. In the context of the instant invention, the bearing surface at issue arises at the interface between the outer surface of the spherical distal end of the tubular inner member of a conventional shaver blade assembly and the corresponding inner surface of the spherical distal end of the tubular outer member of the conventional shaver blade assembly.

The instant invention has both human medical and veterinary applications. Accordingly, the terms "subject" and "patient" are used interchangeably herein to refer to the person or animal being treated or examined. Exemplary animals include house pets, farm animals, and zoo animals. In a preferred embodiment, the subject is a mammal.

Hereinafter, the present invention is described in more detail by reference to the Figures and Examples. However, the following materials, methods, figures, and examples only illustrate aspects of the invention and are in no way intended to limit the scope of the present invention. For example, while the present invention makes specific reference to arthroscopic shaver blade assemblies, it is readily apparent that the teachings of the present invention may be applied to other minimally invasive cutting instruments and are not limited to arthroscopic uses alone. As such, methods and materials similar or equivalent to those described herein can be used in the practice or testing of the present invention.

Prior Art Shavers

FIGS. 1A through 1F depict various views of a prior art shaver 900 having construction of the type typically used for endoscopic shaver blades. Shaver 900 has an inner assembly 910 having a proximal hub assembly 912 with inner hub 914 with drive portion 916, spring retainer 918 and spring 920, spring retainer 918 containing spring 920 being axially movable on inner hub 914 so as to allow compression of spring 920 when shaver 900 is placed in a shaver handpiece. Inner assembly 910 has a tubular distal portion 922 having a proximal end 924 to which inner hub 914 is mounted, and a distal end 926 on which is formed distal hemispherical outer surface 928 and cutting window 930. Shaver 900 further includes an outer assembly 940 having a proximal hub assembly 942 that includes outer hub 944 and retainer 946, and a closed-end distal tubular element 950 having a proximal end 952 to which outer hub 944 is mounted, and a distal end 954 having a hemispherical inner surface 956 and a cutting window 958 formed therein. Inner assembly 910 is rotatably positioned within outer assembly 940, such that the outer diameter of inner tubular element 922 closely conforms to the inner diameter of outer tubular element 950. The distal position of inner assembly 910 is determined by contact between hemispherical outer surface 928 of distal end 926 of inner tubular element 922 and hemispherical inner surface 956 of distal end 954 of outer tubular element 950 which together form a bearing, wherein contact between the bearing surfaces is maintained by spring 920 which is compressed between inner hub 914 and spring retainer 918 in contact with elements of the handpiece (not shown). The radius of the hemispherical inner surface 956 of outer tubular element 950 is slightly larger than that of hemispherical surface outer 928 of inner tubular element 922 so that ideally contact between the surfaces is at a single point.

The single-point nature of the distal bearing is problematic since it creates high Hertzian stresses in surfaces that are subjected to relative rotational motion. Galling and coldwelding may occur unless gall-resistant materials or coatings are used. In U.S. Pat. No. 8,313,502, the contents of which are incorporated herein by reference in their entirety, Heisler describes these phenomena in detail and a construction for endoscopic shavers that eliminate the distal bearing/galling problem by eliminating the distal bearing. Referring now to FIGS. 2A through 2D depicting various views of a prior art shaver embodiment taught by Heisler, wherein like elements are numbered in a fashion analogous to those of FIGS. 1A-1F, element 915, formed from a suitable polymeric or metallic material, is mounted to the distal end portion of inner hub 914 so as to create a bearing between the distal surface of element 915 and a proximal-facing planar surface of outer hub 944. The bearing surfaces are keep in contact by distal force supplied by spring 920. Elimination of the distal bearing eliminates the need for gall-resistant materials at the distal bearing point resulting in significant savings in the manufacturing cost and allows cutting window configurations not possible with previous shaver designs which use a distal bearing.

While Heisler represents a significant breakthrough in shaver construction, further improvements are possible and the subject of the invention herein disclosed.

When cutting tissue becomes trapped between the cutting edges of inner cutting window 930 and outer cutting window 958, distal end 926 of inner member 922 may undergo lateral deflection due to resistance of the tissue to cutting. Moreover, due to wrapping of tissue into the gap between distal portion 926 of inner tubular member 922 and distal portion 954 of outer tubular member 950, such tissue can end up being torn as the edges rotate past each other rather than cut by the edges as is preferred. These lateral forces can be significant, particularly when cutting fibrous tissue such as meniscus or vertebral disc. Deflection of distal portion 926 of inner member 922 frequently causes rubbing of distal portion 926 against the interior surface of distal portion 954 of outer tubular member 950 and may cause galling or cold-welding of the surfaces. The deflection may also cause the cutting edges of cutting windows 926 and 958 to contact each other. In both cases, metallic debris can be produced and deposited into the surgical site, an undesirable condition.

Shavers of the Present Invention Having an Improved Distal Bearing

Endoscopic shavers constructed in accordance with the principles of the present invention are provided with a polymeric bearing immediately proximal to the inner cutting window that minimizes lateral deflection of the distal portion of the inner tubular member during use.

Figure 3A:
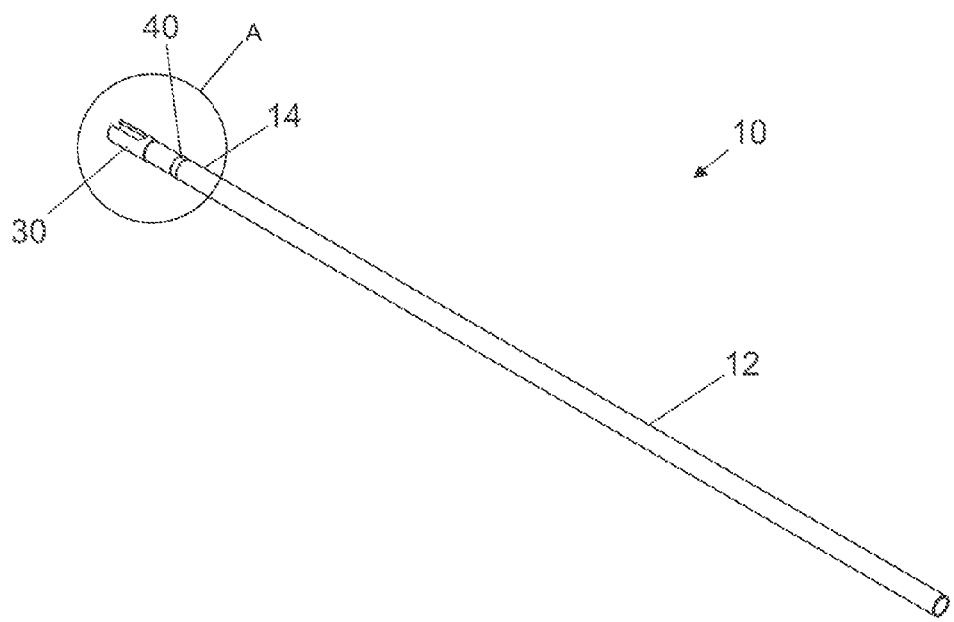
FIGS. 3A to 3E depict various views of an endoscopic shaver formed in accordance with the present invention. In particular.
Figure 3B:
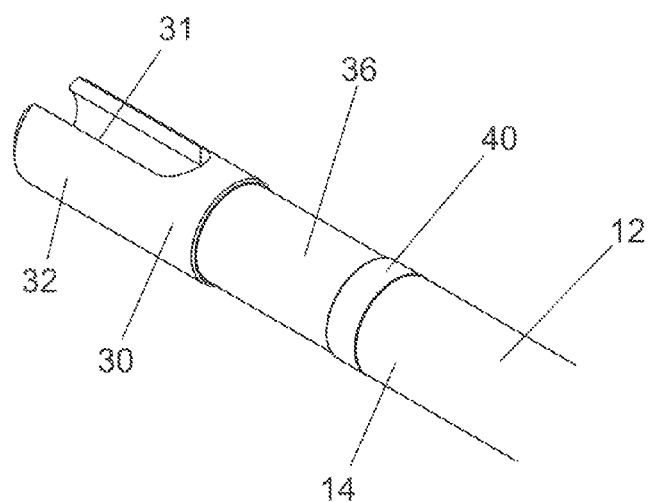
Figure 3C:
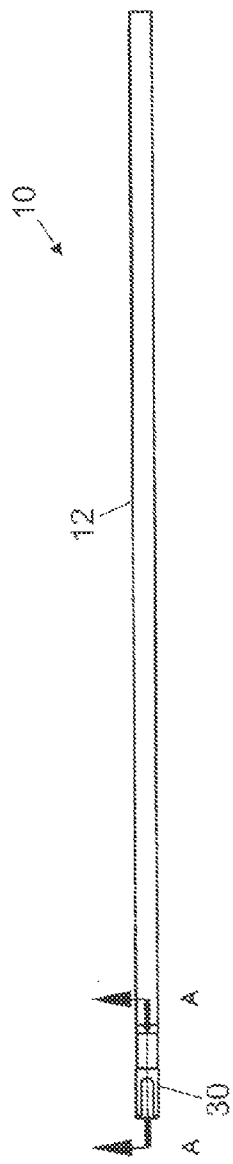
Figure 3D:
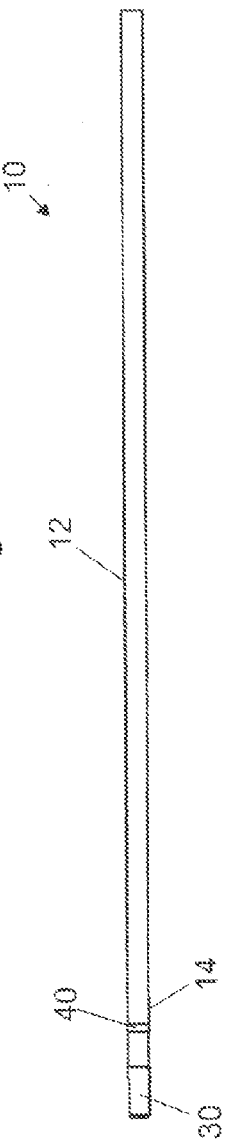
Figure 3E:
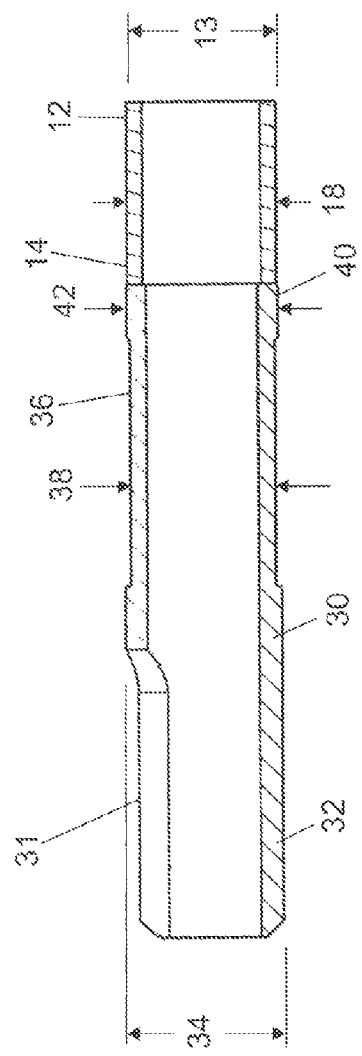
Figure 4A:
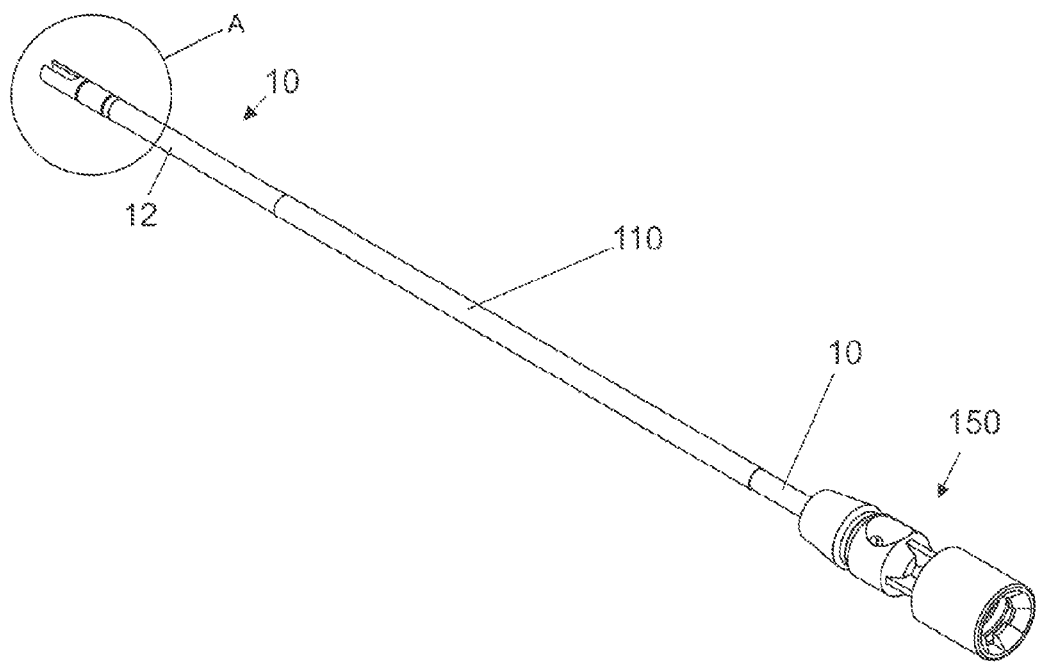
Figure 4B:
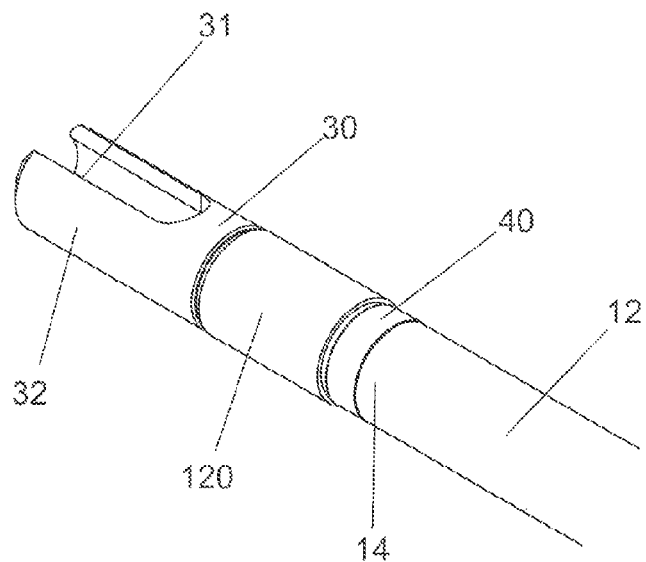

FIGS. 3A through 3E depict various views of the inner assembly 10 of tube 12 and shell 30 for a endoscopic shaver formed in accordance with the principles of this invention. Tube 12 has a distal end 14, affixed to proximal portion 40 of a first shell 30 (referred to herein as the "inner shell") by laser welding, brazing, or other permanent joining method. Tube 12 has an outer diameter 18. Inner shell 30 has a distal portion 32 having formed therein cutting window 31, a mid-portion 36 and a proximal portion 40. As best seen in FIG. 3E, distal portion 32 of shell 30 has a diameter 34; mid-portion 36 has a diameter 38 which is less than diameter 34 of distal portion 32; and proximal portion 40 has a diameter 42 which is greater than diameter 38 of portion 36, but less than diameter 34 of portion 32. Distal end 14 of tube 12 has a diameter 13 less than diameter 42 of proximal portion 40 of shell 30.

FIGS. 4A through 4E depict various views of a further embodiment of an inner assembly 100 of a shaver constructed in accordance with the principles of this invention, wherein like elements are numbered in a fashion analogous to those of FIGS. 3A-3E. Inner assembly 100 has a proximal hub assembly 150 affixed to proximal end 16 of tube 12 and inner assembly 10. The mid-portion 18 of tube 12 (FIG. 3E) is covered by a first polymeric tubular sleeve member 110. Mid-portion 36 of shell 30 (FIG. 3E) is covered by a second polymeric tubular sleeve member 120. In a preferred embodiment, sleeve members 110 and 120 are formed from heat shrink tubing that is heated and shrunk in place. Tubular sleeve members 110 and 120 may be fabricated from PTFE, PEEK, polyolefin, or any other suitable polymeric material. Diameter 122 of polymeric sleeve element 120 is greater than that of diameter 34 of distal portion 32 of shell 30 (FIG. 3E). Diameter 111 of tubular element 110 is greater than diameter 42 of proximal portion 40 of shell 30.

Figure 5A:
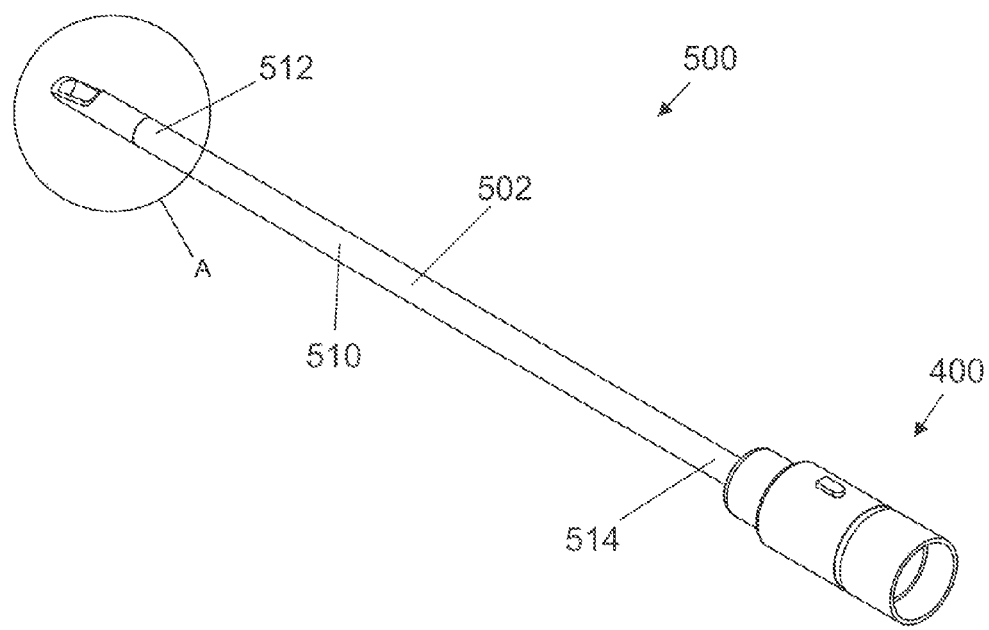
FIGS. 5A to 5E depict various views an outer tubular assembly of an endoscopic shaver formed in accordance with the present invention. In particular.
Figure 5B:
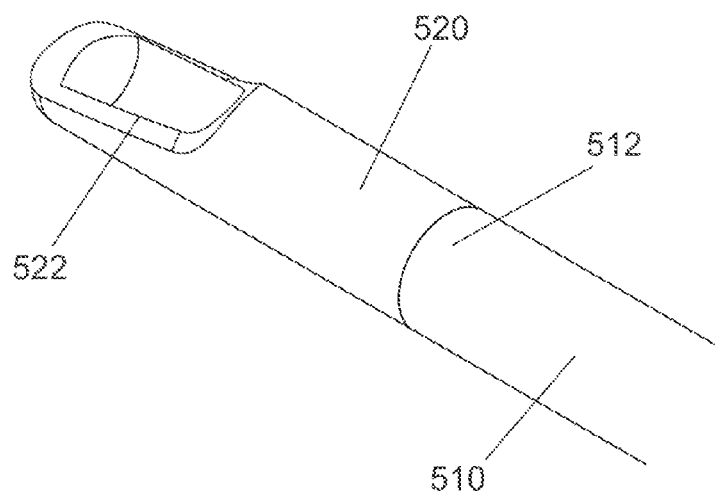
Figure 5C:
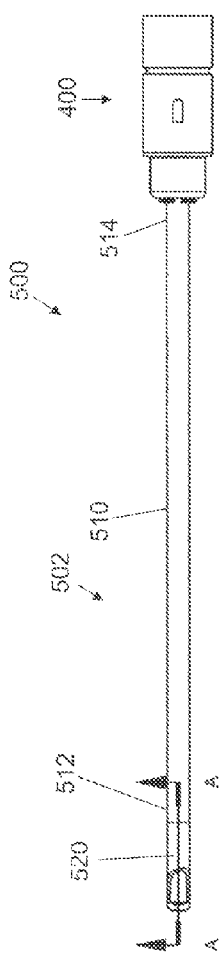
Figure 5D:
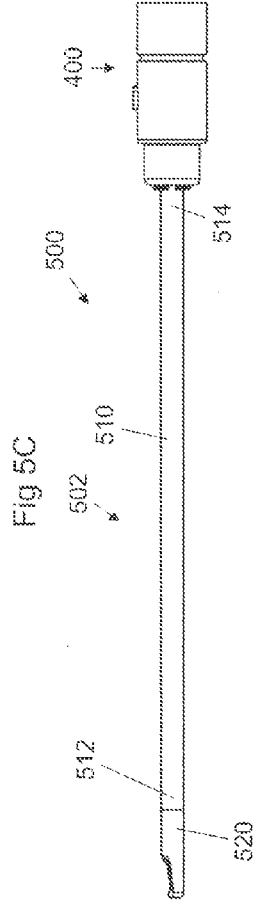
Figure 5E:
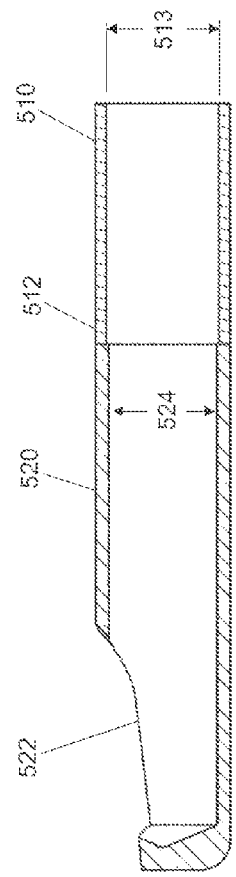
Figure 6A:
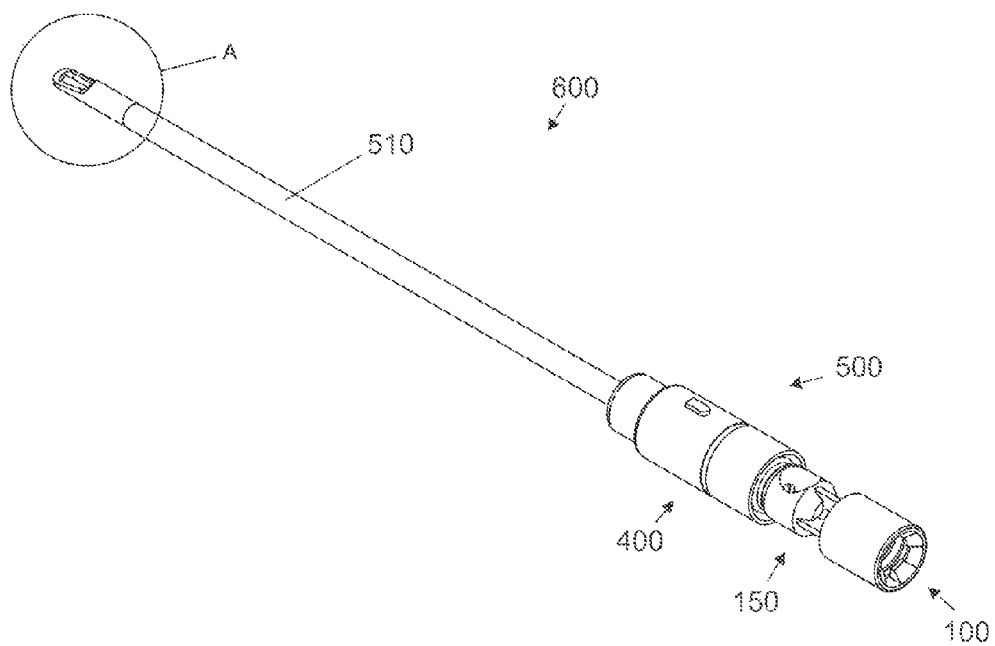
Figure 6B:
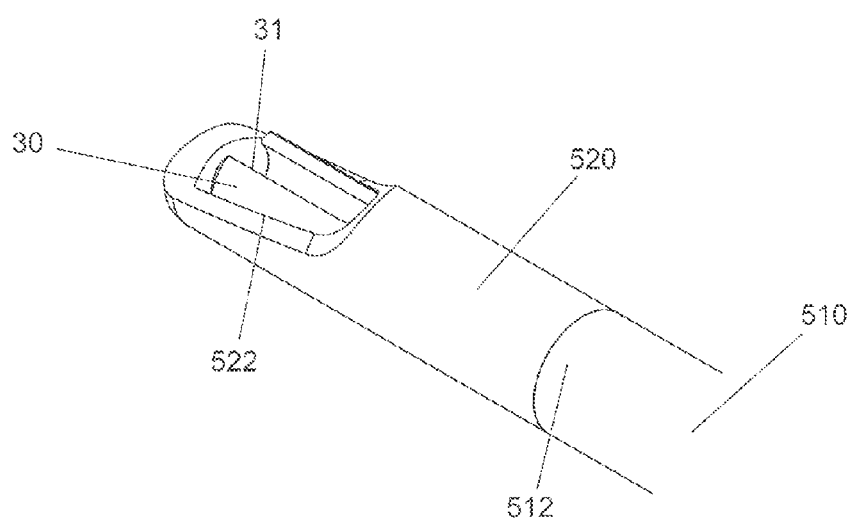
Figure 7:
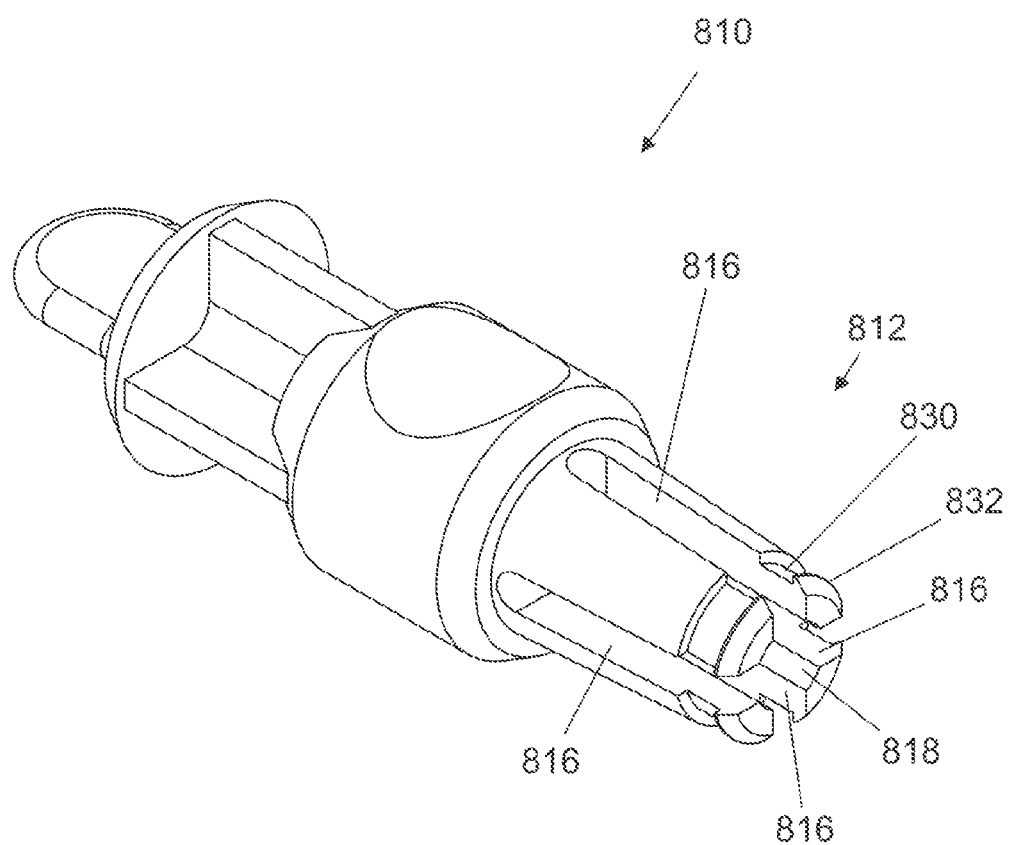
FIG. 7 is a perspective view of an alternate embodiment for inner hub formed in accordance with the principles of this invention.
Figure 8:
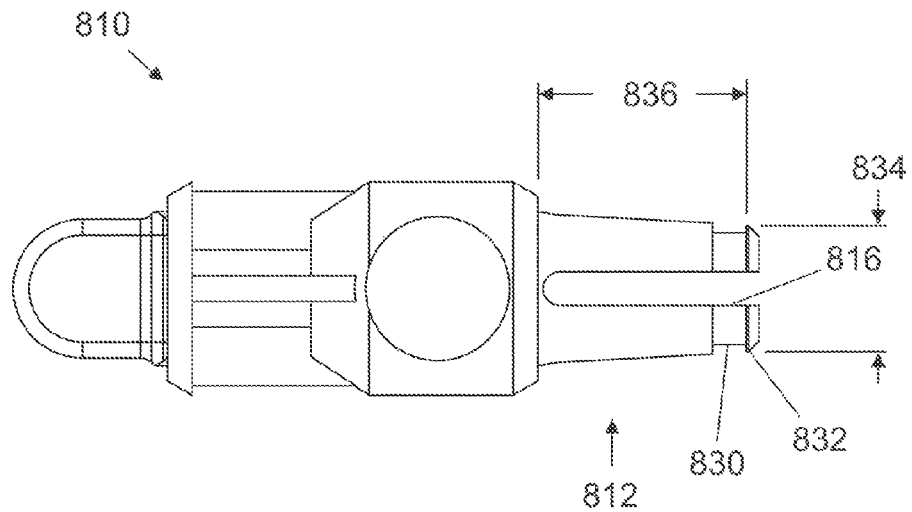
FIG. 8 is a plan view of the objects of FIG. 7.
Figure 9:
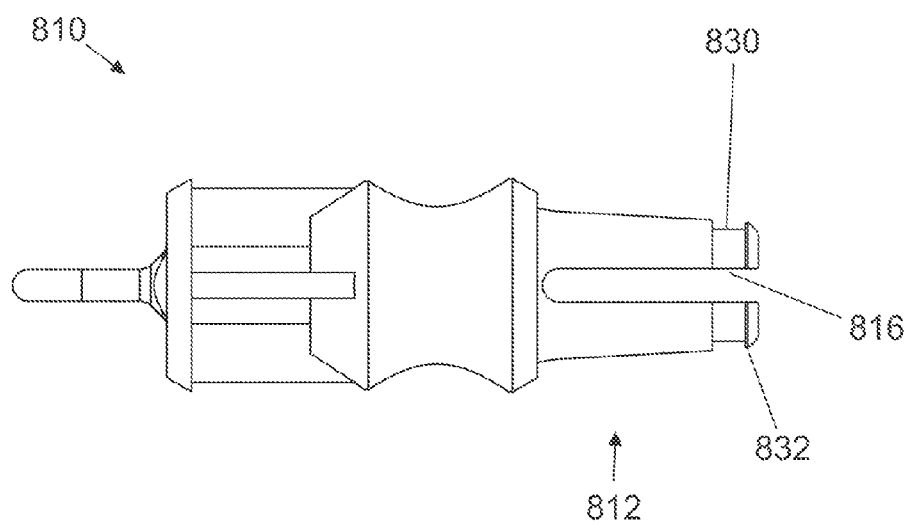
FIG. 9 is a side elevational view of the objects of FIG. 7.
Figure 10:
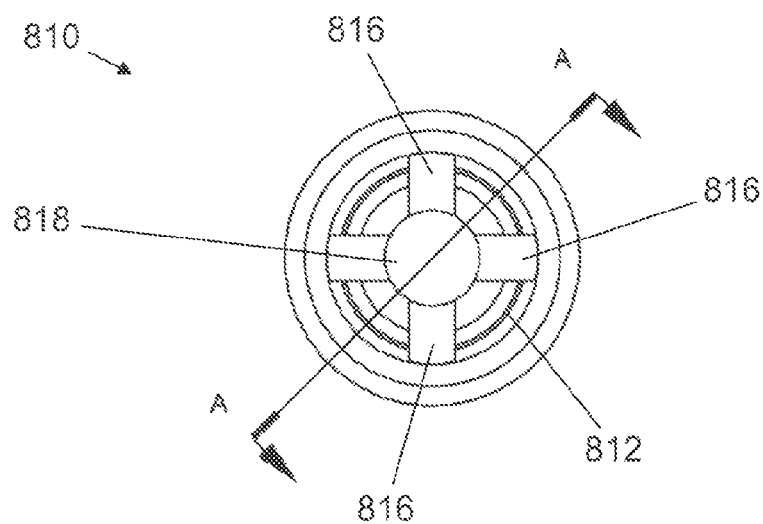
FIG. 10 is a distal axial view of the objects of FIG. 7.
Figure 11:
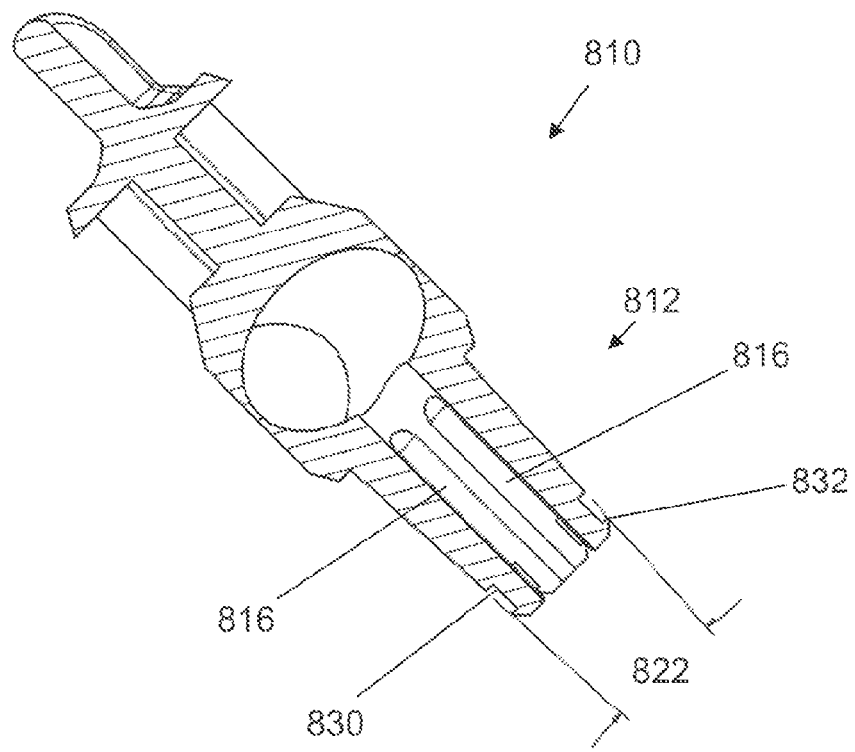
FIG. 11 is a sectional view of the objects of FIG. 7 at location A-A of FIG. 10.
Figure 12:
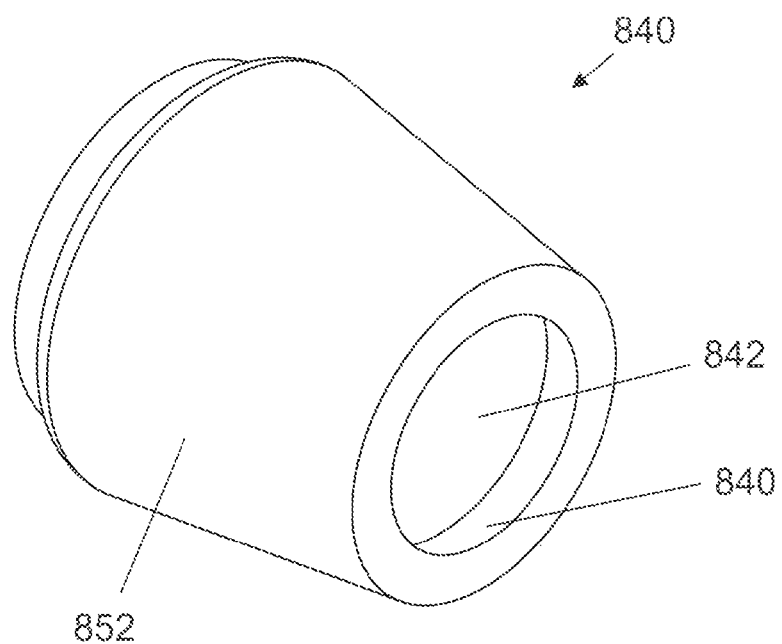
FIG. 12 is a perspective view of a collar for use with the alternate embodiment hub of FIG. 7.
Figure 13:
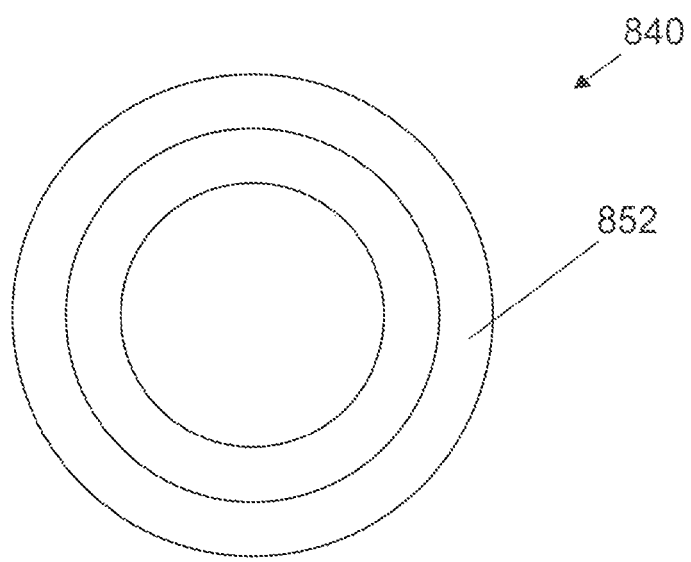
FIG. 13 is a distal axial view of the objects of FIG. 12.
Figure 14:
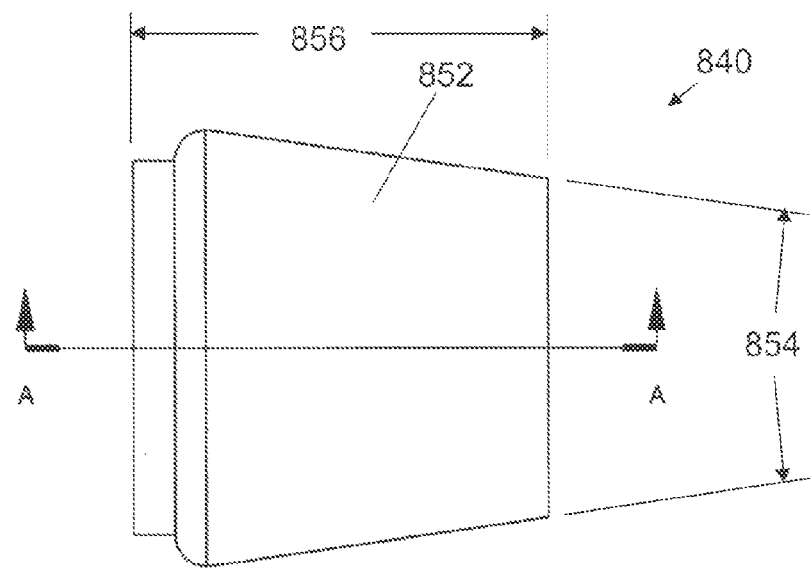
FIG. 14 is a plan view of the objects of FIG. 12.
Figure 15:
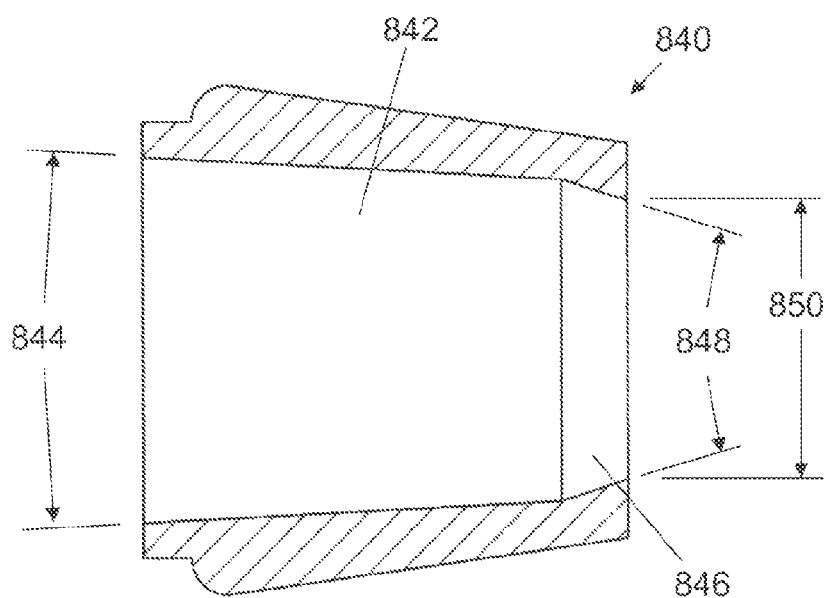
FIG. 15 is a side elevational sectional view of the objects of FIG. 14 at location A-A of FIG. 14.
Figure 16:
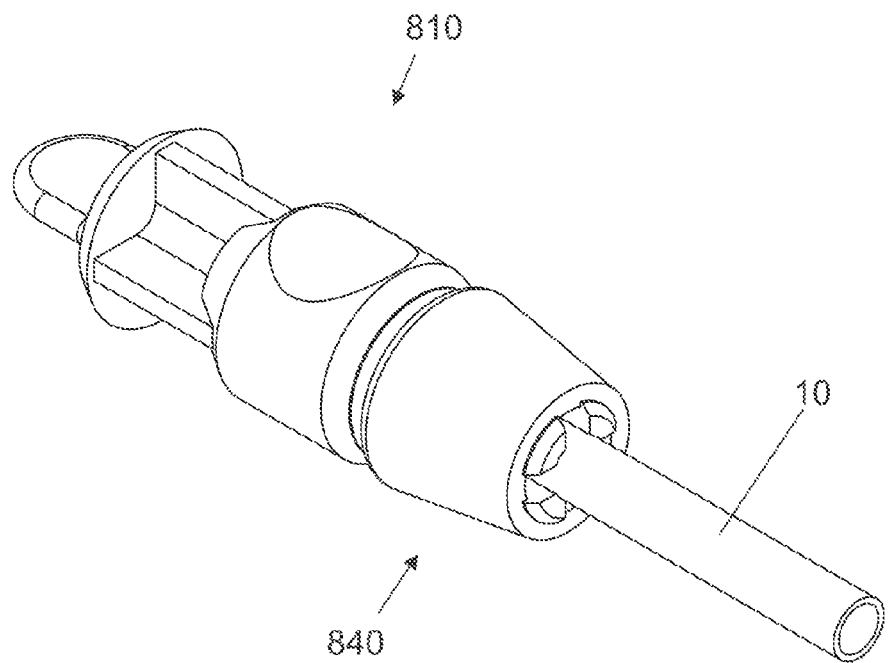
FIG. 16 is a perspective view of the assembly of the alternate embodiment hub of FIG. 7 and collar of FIG. 12 on a tubular member.

FIGS. 5A through 5E depict various views of an outer assembly 500 of a shaver formed in accordance with the principles of this invention, wherein like elements are numbered in a fashion analogous to those of the preceding figures. Outer assembly has a tubular portion 502 comprised of tubular member 510 having a distal end 512 to which is affixed a second shell 520 (referred to herein as the "outer shell") in which is formed cutting window 522. Tubular member 510 has a proximal end 514 to which is mounted outer hub assembly 400. Shell 520 is mounted to distal end 512 of tubular member 510 by laser welding, brazing or any other suitable means of permanent fixation. As best seen in FIG. 5E, outer shell 520 has an inner diameter 524 which is less than diameter 513 of tubular member 510.

FIGS. 6A through 6E depict various views of an assembled shaver 600 formed in accordance with the principles of this invention, wherein inner assembly 100 is rotatably positioned within outer assembly 500. As with previous figures, analogous elements of FIGS. 6A through 6E are numbered in a fashion analogous to those of the preceding figures.

FIG. 6E depicts the distal end portion of assembled shaver 600. Because outer diameter 122 of tubular polymeric member 120 (FIG. 4E) is greater than outer diameter 34 of distal portion 32 of inner shell 30 (FIG. 3E), contact between inner shell 30 and outer shell 520 is prevented, with polymeric member 120 forming a lubricious bearing between the distal end shells of the inner and outer assemblies. In a similar manner, tubular polymeric member 110 (FIG. 4E) prevents contact between inner tubular member 10 and outer tubular member 500. Polymeric member 110 also limits flexing of inner tubular member 10 within tubular member 500 when shaver 600 is cutting tough fibrous tissue like meniscus or vertebral disc, thereby preventing contact between the edges of inner cutting window 31 of inner shell 30 and the edges of outer cutting window 522 of outer shell 520.

Outer shell 520 and inner shell 30 are precisely machined elements that are maintained in relative concentricity by polymeric element 120 which acts as a bearing so as to prevent contact between the shells. Because there is a gap between outer shell 520 and distal end 14 of inner tubular member 12 to which proximal portion 40 of inner shell 30 is joined, extreme precision in the concentricity of the joining method is not required. Distal end 14 of inner tubular member 12 may be eccentric with regard to inner shell 30 so long as the eccentricity does not cause contact between member 12 and outer shell 520. Indeed, the outer diameter 13 of inner tubular member 12 (FIG. 3E) is unimportant so long as it is less than diameter 42 of proximal portion 40 of inner shell 30 since the concentricity of the shells is determined by distal polymeric bearing 120. Because diameter 13 is not critical to the functioning of shaver 600, widely available standard gauge hypodermic tubing may be used for inner tubular member 12 in contrast to the higher cost, specially produced tubing required by prior art shavers 900. This is expected to result in significant cost savings. Similarly, referring to FIG. 5E and FIG. 6E, so long as diameter 513 of outer tubular member 512 is greater than inner diameter 524 of outer shell 520, the diameter 513 is unimportant so that a standard gauge hypodermic tubing may be used for outer tubular member 512 in contrast to the custom manufactured tubing required by the prior art thereby resulting in reduced manufacturing costs. Further, as best seen in FIG. 6E, because there is a gap between the outer surface of inner tubular member 12 and the inner lumen of outer tubular member 510, extreme straightness is not required for the tubular members as is the case with prior art shavers 900. Moreover, polymeric member 110 of inner assembly 100 prevents contact between the tubular members if there is a significant bend in either of or both of the tubular members.

Endoscopic shavers of the present invention are constructed so as to be tolerant of variations in materials and in the manufacturing processes. Because the concentricity of inner shell 30 and outer shell 520 is maintained by polymeric bearing 120 and is independent of the straightness and size of outer tubular member 510 and inner tubular member 12, variations in tubing size and straightness may be accepted without affecting the function of shaver 600. Because the concentricity of the shells is independent of the concentricity of the joining operation of outer shell 520 to outer tubular member 510 or of inner shell 30 to inner tubular member 12, variations in concentricity due to the joining process can be tolerated. Machining of the outer surface of inner shell 30 after joining to inner tubular member 12 to ensure precise concentricity is not required. This is also expected to result in reduced manufacturing costs.

Referring to FIGS. 4A through 5D, in another contemplated embodiment, the assembly of outer tubular member 510 and outer shell 520 may be integrated into and thus replaced by a single element that is a closed end tube having a far distal portion that has a reduced inner diameter. This reduced portion may have an inner lumen that is formed to a predetermined diameter by reaming or drilling so as to be functionally analogous to outer shell 520, the larger diameter portion of the tube being analogous to tubular member 510. So long as the inner assembly is formed form an elongate tubular member to which is affixed a shell having a reduced mid-portion in which a polymeric element is positioned to act as a bearing between the inner and outer shells, the endoscopic shaver is within the scope of this invention.

Shavers of the Present Invention Having Improved Hub Connection

Inner assembly 100 of FIGS. 4A-4E has a proximal hub assembly 150 affixed to proximal end 16 of tube 12 of tube and distal end shell assembly 10 and tubular member 510 of outer assembly 500 of FIGS. 5A-5E has a proximal end 514 to which is mounted outer hub assembly 400. In prior art shaver 900 of FIGS. 1A-1F and others, inner hub 914 is mounted to proximal end 914 of tubular member 922, and outer hub 944 is mounted to proximal end 952 of outer tubular member 950 by heating the proximal ends of the members and forcing them into a lumen of the respective hub. The hub mounting operation, accomplished in a machine commonly called an "induction bonder" or simply "bonder", uses an induction heater to locally heat the proximal end of the tube to a high temperature, after which it is forced at a rapid rate into the lumen of the hub. This hub mounting process has several drawbacks. First, it requires an induction heater with its associated chiller to provide cooling water for the heater. Second, it requires a precise bonding fixture to ensure that the hubs and tubes are in proper alignment prior to bonding and are in the proper axial relationship when bonding is completed. During setup of the induction bonder, as when changing from one size or type of shaver to another, numerous hubs and tube and shell assemblies are discarded since the axial relationship of the hubs must be tightly controlled and setup is done using an iterative, trial and error method. The cost of the setup process may, therefore, be significant due to wasted components. Additionally, the bonding process is slow due to the time required for loading of the hubs and tube assemblies into the bonding fixture, for heating of the tube proximal end to a high temperature, and for unloading of the finished assembly from the bonding fixture.

Endoscopic shavers constructed in accordance with the principles of the present invention can include hubs that do not require an induction bonder for mounting the hubs to the tube assembly proximal ends. Rather, in accordance with a preferred embodiment, a polymeric collar having a tapered conical inner surface matching a conical outer surface on the distal portion of the hub can be applied to the distal portion of the hub so as to cause a compressive force in the inner lumen of the hub. The hub distal portion can then be provided with slots formed therein which allow it to grip a tubular member placed in its lumen, with the distal portion functioning in the same manner as a collet when the collar is assembled axially onto the distal portion.

Such an alternate embodiment inner hub 810 configured for use with such a polymeric collar is depicted in FIGS. 7 through 11. Inner hub 810 is analogous to hubs previously described except as noted herein. In particular, hub 810 has a conical tubular distal portion 812 of included angle 822 wherein are formed slots 816 that intersect lumen 818. Distal portion 812 has formed therein a circumferential slot 830 near its distal end 832 of diameter 834. The distal wall of circumferential slot 830 is displaced a distance 836 from the proximal end of conical distal portion 812.

FIGS. 12 through 15 depict a polymeric collar 840 having a lumen 842 with a first conical portion 842 with included angle 844 equal to included angle 822 of distal portion 812 of inner hub 810, and a second conical portion 846 with an included angle 848 and distal-most diameter 850 which is less than diameter 834 distal end 832 of distal portion 812 of hub 810. Conical outer surface 852 has an included angle 854. Ring 840 has an axial length 856 which is slightly less than distance 836 of distal portion 812 of hub 810. Ring 840 has a distal-most surface 858.

FIGS. 16 through 19 depict the polymeric collar 840 of FIGS. 12 to 15 assembled to inner hub 810 of FIGS. 7 to 11 so as to grip inner tube 10 in accordance with the principles of this invention. Assembly is accomplished in the following manner: proximal end 16 of inner tube 10 is axially positioned within lumen 818; collar 840 is pressed onto distal portion 812 of hub 810 until distal-most surface 858 of collar 840 is within groove 830 so as to prevent removal of collar 840 from distal portion 812 of inner hub 810. Conical distal portion 812 of hub 810 and first conical portion 842 of collar 840 are sized such that when collar 840 is assembled to hub 810, the diameter of lumen 818 is reduced to that of tubular member 10 and compressive force created sufficient to maintain axial positioning of the tubular member 10 within hub 810 and to transmit torque to tubular member 10 during use in a shaver. In a preferred embodiment, proximal end of tubular member 10 is knurled so as to aid the gripping of tubular member 10.

Also contemplated is an alternate embodiment wherein the second conical section 846 of collar 840 and the groove 830 of hub 810 are eliminated. In this instance, the respective Luer-like tapers, arising from angle 822 of distal portion 812 of hub 810 and angle 844 of collar 840, form a self-locking connection such that when collar 840 is forced axially onto distal portion 812 of hub 810 friction forces between the complimentary surfaces are sufficiently high to prevent disassembly.

Mounting hub 810 to tube 10 is accomplished in the following manner. Tubular member 10 is inserted into lumen 818 of hub 810 and collar 840 is positioned on tubular member 10 distal to hub 840. The unassembled elements are placed into a fixture in which hub 810 is held in a first nest cavity by a clamping means and tubular member 10 is held in a second nest cavity with features to position hub 810 in a predetermined axial position on tube 10. Collar 840 is then forced onto conical distal portion 842 of hub 810 so as to constrict the distal portion of lumen 818 of hub 810 about tube 10. The finished assembly is then unclamped and removed from the fixture. Assembly by this method has advantages over the assembly of prior art hubs using an induction bonder. The fixture of the current embodiment is purely mechanical (i.e., friction fit) and requires no heating of the tubular member. Therefore the need for an induction heater may be eliminated. Furthermore, no parts are wasted during setup of the assembly fixture since trial and error iterative setup is also eliminated. The purely mechanical fixture has predetermined features (i.e., nests) that position hub 810 and tube 10 in their desired axial relationship before collar 840 is assembled to hub 810. The decreased setup time and lack of wasted parts during setup is expected to result in a decrease in manufacturing costs.

Figure 20:
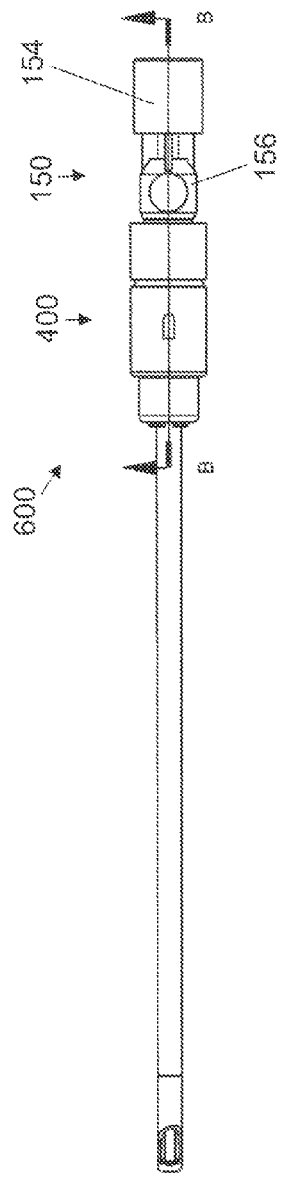
FIG. 20 is a plan view of an alternate hub assembly for a shaver constructed according to the instant invention.
Figure 21:
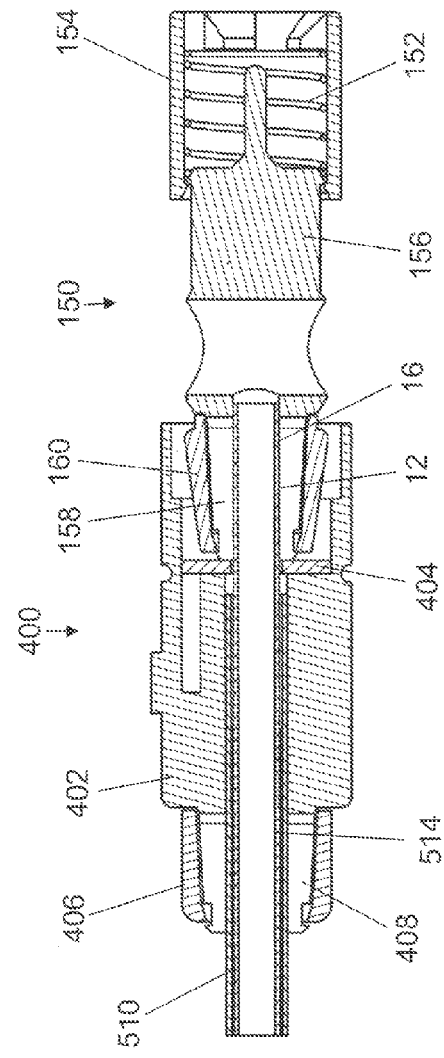
FIG. 21 is an expanded sectional view of the elements of FIG. 20 at location A-A.

The embodiment configuration of hub 810 is illustrated using an inner hub, but may be advantageously applied to outer hubs as well. FIGS. 20 and 21 depict inner hub assembly 150 and outer hub assembly 400 of shaver 600 in which like elements are numbered in a fashion analogous to those of the preceding figures. Inner hub assembly 150 includes a spring 152 and spring retainer 154 as is conventional in the prior art construction. Inner hub assembly 150 further includes inner hub 156 that is also of conventional construction with the exception that the distal portion 158 is formed as in hub 810 previously herein described, and collar 160 that is formed in like manner to collar 840 previously herein described. Collar 160 is positioned on distal portion 158 as previously herein described so as to grip knurled proximal end 16 of tubular member 10. Outer hub assembly 400 includes outer hub 402, bearing 404 and collar 406. Hub 402 is like hub 944 of shaver 900 except that bearing 404 is mounted in hub 402 as shown, and hub 402 has a tapered distal portion 408 that is functionally equivalent to distal portion 158 of inner hub 156. Collar 406 functions in the same manner as collar 160 of inner hub assembly 150, being positioned on distal portion 408 of outer hub 402 so as to grip knurled proximal end 514 of tubular element 510.

Shavers of the Present Invention Having an Improved Bendability

The inventors have discovered that using a distal tubular member with non-uniform flexural strength throughout its length allows the bending of the tube at distal locations not only to an initial small radius bend, but rebending as required to other angles with all bends occurring in the same distal region. Specifically, when a portion of the tube near its distal end has its flexural strength reduced, an initial small-radius bend and angular offset may be produced in the tubular member by the surgeon as needed to enable access to a target tissue site, and the surgeon can modify the angular offset subsequently to access other sites through the use of a manual bending device. The angular offset of the tube distal end may be modified by altering the degree of bend with the deformation of the tube remaining localized in the bend region since adjacent portions of the tube have a higher flexural strength. The flexural strength in the bend region may be reduced by notching the tube in the bend region, by annealing the tube in the bend region, by reducing the wall thickness in the bend region, or by any combination of these means. All such combinations are considered to fall within the scope of this invention.

FIGS. 22 through 24 depict an illustrative inner distal tubular assembly 702 for a rebendable shaver formed in accordance with the principles of the instant invention. Inner tubular assembly 700 has a distal shell 702 configured like inner shell 30 (FIG. 3E) but elongated for the instant embodiment. Shell 702 has a distal cutting window 703 and a proximal end 704 which is affixed by welding, brazing or another method to distal end 708 of flexible tubular member 706. Proximal end 710 of flexible tubular member 706 is joined by welding, brazing or another method to distal end 714 of rigid tubular member 712. Shell 702 has positioned in its reduced diameter mid-region polymeric tubular member 716 that forms a bearing. The mid-portion of rigid tubular member 712 is covered by polymeric member 718. Optionally, flexible tubular member 706 may also be covered by a polymeric member.

FIGS. 25 through 29 depict an illustrative outer distal tubular assembly 730 for a rebendable shaver formed in accordance with the principles of the instant invention. Outer tubular assembly 730 has a rigid proximal tubular assembly 732 having a proximal end 734 and a distal end 736, adjacent to which are formed notches 738 spaced distance 739 apart, the notches 738 on opposing sides being axially offset such that slots 738 on a first side are axially positioned to be centered between slots 738 of a second side. Outer shell 740 has a proximal end 742 that is affixed by welding, brazing or other method to distal end 736 of tubular member 732. Shell 740 has a distal end 744 having a cutting window 746 formed therein. Inner diameter 748 of shell 740 is sized to be less than inner diameter 750 of tubular portion 732.

Figure 25:
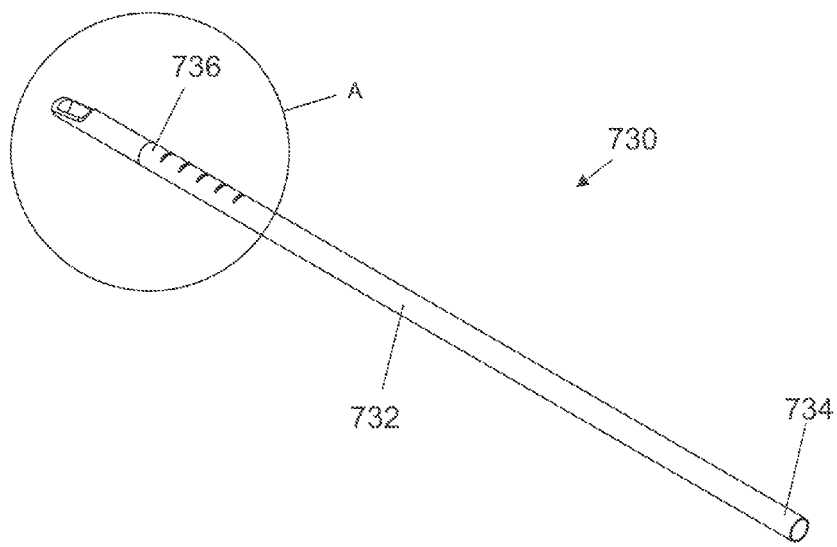
FIG. 25 is a perspective view of the outer tubular assembly for an alternate embodiment rebendable shaver of the instant invention.
Figure 26:
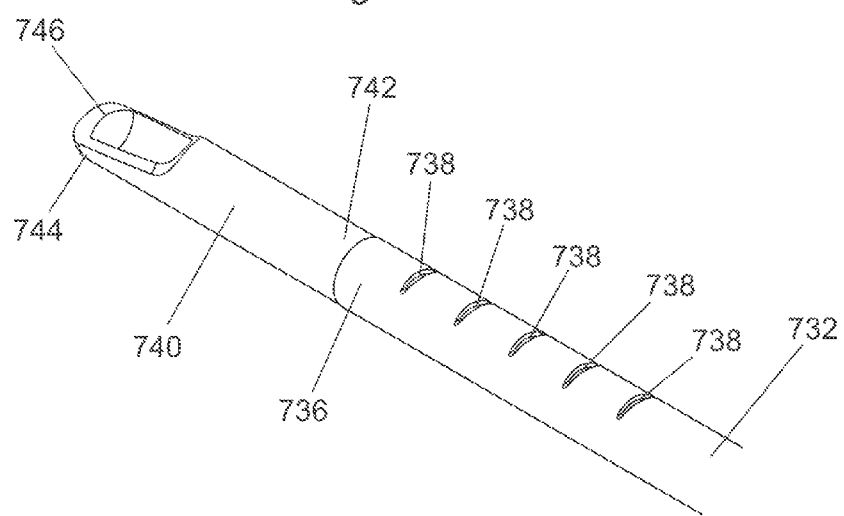
FIG. 26 is an expanded perspective view of the distal portion of the objects of FIG. 25 at location A.
Figure 39:
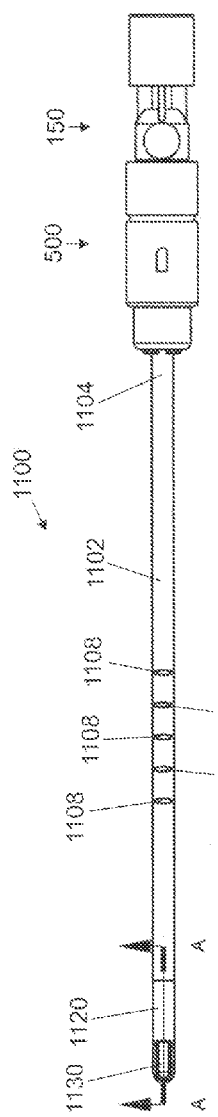
FIG. 39 depicts an alternate embodiment of an endoscopic shaver formed in accordance with the instant invention during manufacture.
Figure 40:
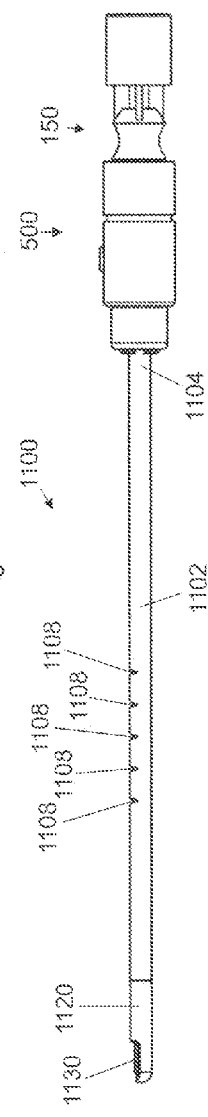
FIG. 40 is a side elevational view of the objects of FIG. 39.
Figure 41:
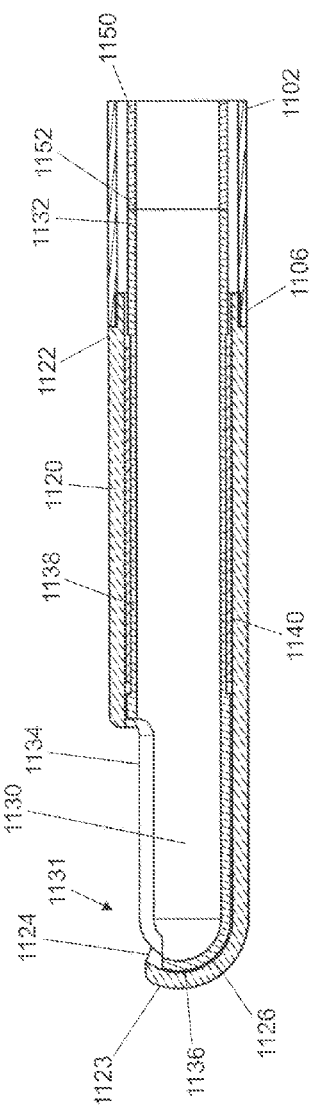
FIG. 41 is an expanded sectional view of the objects of FIG. 39 at location A-A.
Figure 42:
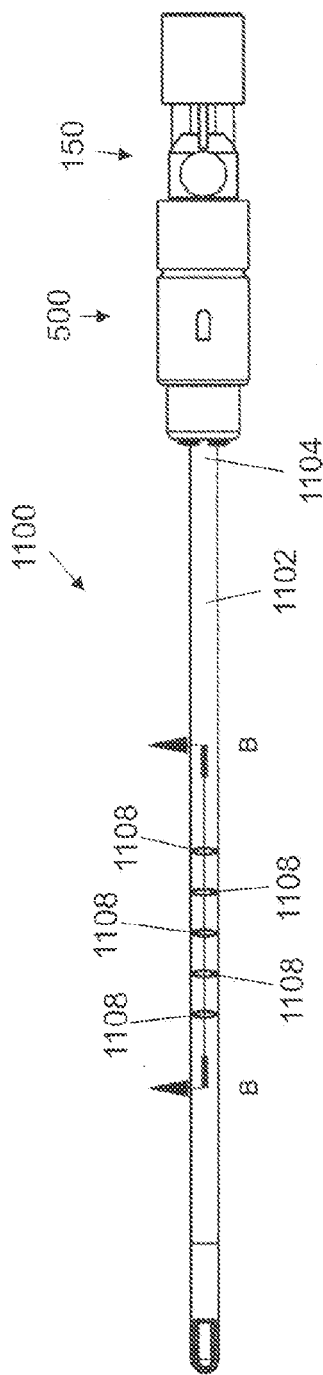
FIG. 42 is a plan view of the objects of FIG. 39.

FIGS. 30 through 32 depict a rebendable endoscopic shaver 760 formed in accordance with the principles of the instant invention, with inner tubular assembly 702 of FIG. 22 being rotatably positioned within outer tubular assembly 730 of FIG. 25. Inner hub assembly 150 is affixed to proximal end 716 of inner tubular member 718 of inner tubular assembly 702. Outer hub assembly 500 is affixed to proximal end 734 of tubular element 732 of outer tubular assembly 730. Tubular polymeric member 750 covers tubular element 732 of outer tubular assembly 730. As best seen in FIG. 32, flexible element 716 is positioned axially within the distal portion of outer tubular member 732 having notches 738. Polymeric member 716 functions as a bearing between inner shell 702 and outer shell 740. Polymeric member 718 prevents rubbing between inner tubular member 712 and outer tubular member 732.

FIGS. 33 through 35 depict endoscopic shaver 760 having its distal portion formed to a first angle 762. The bend is localized in the portion of outer tubular member 732 wherein notches 728 have reduced the flexural strength of tubular member 732. Notches 728 on the convex side of the bend have increased in width while notches 728 on the concave side of the bend have decreased in width. Cutting window 746 of outer shell 740 and cutting window 703 of inner shell 702 are oriented toward the concave portion of the bend.

FIGS. 36 through 38 depict endoscopic shaver 760 having its distal portion reformed to a second angle 764. The bend is localized in the portion of outer tubular member 732 wherein notches 728 have reduced the flexural strength of tubular member 732. Notches 728 on the convex side of the bend have increased in width while notches 728 on the concave side of the bend have decreased in width. Cutting window 746 of outer shell 740 and cutting window 703 of inner shell 702 are oriented toward the convex portion of the bend.

Notches 728 in tubular member 732 are laterally opposed so that the distal portion of tubular member 732 may be bent either upward or downward. In other embodiments notches 728 may be positioned on only one side of the tube, notches on the top surface allowing upward bending only, and notches on the bottom side allowing downward bending only. Alternatively, in some cases it may be desirable to have the bends in the lateral plane of the device, a configuration achieved by positioning the notches in that plane. All are within the scope of this invention since all are produced by locally reducing the flexural strength of tubular element 732.

The rebendable endoscopic shaver 760 uses a tubular member having non-uniform flexural strength provided by notching of the portion of outer tubular member 732 that is to be bent. In other embodiments, the localized reduction in flexular strength may be achieved by reducing the wall thickness of the tube in the region, or by locally annealing the region, as with, for instance, an induction heater.

While the embodiments herein described have a tubular inner member which is not a closed end tube, alternate embodiment shavers have conventional closed-end inner and outer tubular members, such shavers being within the scope of this invention. Similarly, the embodiments herein described have a proximal bearing located between the inner and outer hub assemblies to establish the axial position of the inner assembly relative to the outer assembly. In other anticipated embodiments the relative axial position may be established by a distal bearing between the distal-most surface of the inner tubular member and the distal inner surface of the outer tubular member. Such embodiments benefit from the polymeric bearing located proximal to the cutting window on the inner shell since it resists lateral forces which may cause galling of the distal portions of the inner and outer members in that region.

Figure 43:
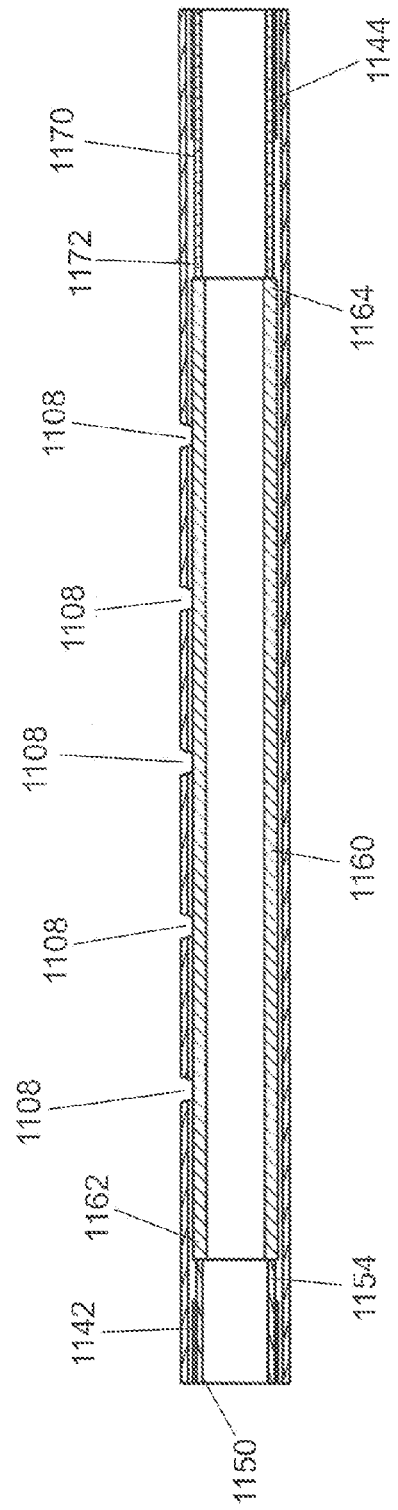
FIG. 43 is an expanded sectional view of the objects of FIG. 42 at location B-B.

FIGS. 39 through 43 depict an alternate embodiment shaver 1100 of the instant invention which does not use a proximal bearing (see FIG. 21, element 404) like the embodiments previously herein described but rather has a distal bearing formed by the distal-most surface of the inner tubular assembly and the proximal facing inner surface of the outer tubular assembly. Also, shaver 1100 is formed to an initial angular offset when supplied to the user, the user subsequently being able to modify this initial angle as required for optimal access to tissue structures. Shaver 1100 has proximal hub assemblies 500 and 150 formed in the usual manner, an outer tubular member 1102 having a proximal end connected to outer hub assembly 500, and a distal end 1106 affixed by welding, brazing or another method to proximal end 1122 of outer shell 1120. Tubular member 1102 has formed in its exterior surface angular notches 1108 extending from the outer surface through the wall of tubular member 1102 into the inner lumen. Shell 1120 has a distal end 1123 having a hemispherical inner surface 1126 and a cutting window 1124. Inner shell 1130 has a proximal end 1132 affixed by welding, brazing, or another method to the distal end 1152 of rigid tubular member 1150. Inner shell 1130 has a distal end 1131 with a distal-most hemispherical surface 1136 and a cutting window 1134. Proximal to cutting window 1134, inner shell 1130 has a mid-portion of reduced diameter 1138 in which is positioned tubular polymeric member 1140 which forms a bearing between inner shell 1130 and outer shell 1132. Inner hemispherical surface 1126 of outer shell 1120 and distal-most hemispherical surface 1136 of inner shell 1130 cooperatively act as a bearing so as to establish the axial position of inner shell 1130 and its associated inner assembly. Referring to FIG. 43, proximal end 1154 of rigid tubular member 1150 is affixed by welding, brazing, or another attachment method to distal and 1162 of flexible tubular member 1160. Flexible member 1160 is attached at its proximal end 1164 to distal end 1172 of rigid tubular member 1170, which has its proximal end affixed to inner hub assembly 150 so as to transmit rotational motion to the inner assembly made up of rigid tubular member 1170, flexible tubular member 1160, rigid tubular member 1150 and inner shell 1130. Rigid tubular member 1150 has positioned near its proximal end 1154 polymeric sleeve 1142 which prevents contact between rigid tubular member 1150 and outer tubular member 1102. Rigid tubular member 1170 has positioned proximal to its distal end 1172 polymeric sleeve 1144 which prevents contact between member 1170 and outer tubular member 1102. The portion of tubular member 1102 distal to outer hub assembly 500 may be covered by a polymeric sleeve, the sleeve extending to a distance distal to slots 1108 but proximal to cutting window 1124 of outer shell 1120.

FIGS. 44 and 45 depict an alternate rebendable shaver embodiment 1100 with its distal portion formed to an initial angular offset 1170. In a preferred embodiment, offset 1170 is formed during manufacture and approximates a preferred angle for a given procedure, such as, for instance, for endoscopic sinus surgery in which large angular offsets are required to access structures under direct visualization. Angular slots 1108 on the concave portion of the bent region of outer tubular member 1102 have decreased in width and reach total closure at angular offset 1170, reopening only slightly due to elastic recovery of tubular member 1102.

Figure 46:
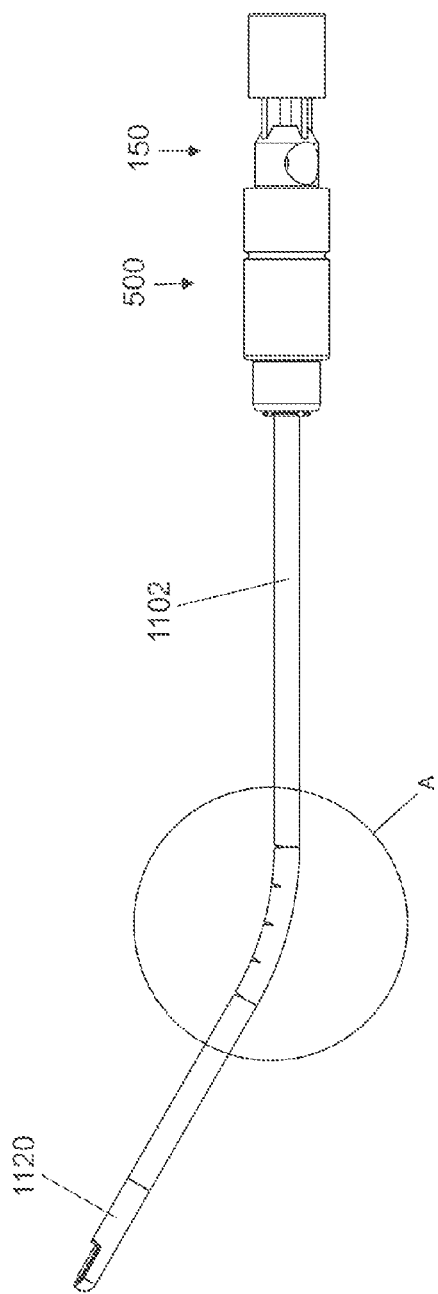
FIG. 46 is a side elevational view of the alternate embodiment shaver of FIG. 39 having its distal portion angularly offset to a second angle through rebending by a user.
Figure 47:
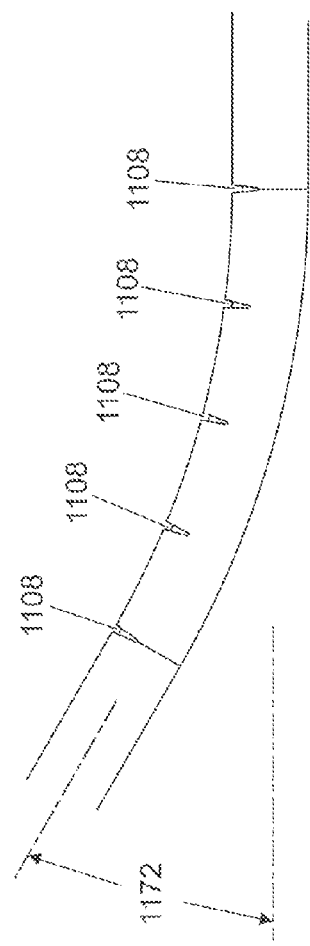
FIG. 47 is an expanded view of the objects of FIG. 46 at location A.

FIGS. 46 and 47 depict shaver 1100 with its distal portion formed (rebent) to a second angular offset 1172 as may be done by a surgeon for optimal access to a tissue structure. Slots 1108 on the concave portion of the bent region of outer tubular member 1102 have increased width. Shaver 1100 may be rebent to other required angular offsets as required during a procedure with all of the bends remaining localized in the region of slots 1108 since the flexural strength of tubular member 1102 has been reduced in that region by slots 1108.

Shaver 1100 is depicted as having an outer tubular member 1102 of unitary construction. However, it may be advantageous in some circumstances to have an outer tubular member that is made of coaxial joined tubular elements that together form an outer tubular member. Such an alternate embodiment is depicted in FIGS. 48 through 50, in which a shaver 1200 is formed in accordance with the principles of the instant invention in which tubular member 1102 of shaver 1100 is replaced by an outer tubular assembly. Distal tubular element 1101 is joined at its proximal end to distal end 1115 of middle tubular element 1113, which is joined at its proximal end 1117 to the distal end of proximal tubular element 1103. Slots 1108 are formed in middle tubular element 1113 in the same manner as in tubular element 1102 of shaver 1100. Shaver 1200 functions in the same manner as shaver 1100 previously herein described. As best seen in FIG. 50, the outer assembly made up of tubular elements 1101, 1113, and 1103 wherein middle tubular element 1113 has a larger diameter than tubular elements 1101 and 1103 allow more clearance for flexible tubular member 1106 so as to prevent constriction of flexible tubular element 1106 if middle tubular element 1113 becomes distorted during bending. For shaver 1200, middle tubular member 1113 is of the same alloy as tubular elements 1101 and 1103 which it overlaps at its distal ends 1115 and 1117 and to which it is joined by welding, brazing or another method. In other embodiments middle tubular member 1113 is of a different alloy from tubular elements 1101 and 1103, the alloy being selected for improved bending or shape retention qualities, for instance, by having a different hardness.

INDUSTRIAL APPLICABILITY

As noted previously, the present invention is directed to minimally invasive endoscopic cutting instrument having improved efficiency, access and reduced manufacturing costs. In particular, by eliminating or modifying the distal end axial bearing surfaces, the present invention provides for a substantial reduction in manufacturing costs as well as a reduced opportunity for galling and metal shedding. Manufacturing costs may be alternatively or further reduced through the use of an improved hub attachment method described herein. In yet a further embodiment, the present invention provides for improved in-field bendability, which, in turn, enables improved access to remote surgical targets.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

The invention has been illustrated by reference to specific examples and preferred embodiments. However, it should be understood that the invention is intended not to be limited by the foregoing description, but to be defined by the appended claims and their equivalents.

What is claimed:

1. An endoscopic cutting instrument comprising:
   a. an outer assembly comprised of an elongate first tubular member having a proximal end configured for attachment to a first proximal hub assembly and a distal end having a first tubular shell configured thereto, wherein said first tubular shell has a first cutting aperture formed in its distal end, further wherein a central lumen extends between the proximal end of said first tubular member and the distal end of said first tubular shell; and
   b. an inner assembly slidably received within the central lumen of said first tubular member, wherein said inner assembly comprises an elongate second tubular member having a proximal end configured for attachment to a second proximal hub assembly and a distal end having a second tubular shell affixed thereto, wherein said second tubular shell is comprised of (i) a proximal portion having a first diameter, (ii) a mid-portion having a second diameter and (iii) a distal portion having a third diameter and a second cutting aperture formed therein;
   further wherein the second tubular member and said second tubular shell are relatively sized such that the diameter of the second shell distal portion is greater than the diameter of the second shell proximal portion which is greater than the diameter of the second shell mid-portion and the distal end of said second tubular member has a diameter that is less than the diameter of the second shell proximal portion;
   further wherein said mid-portion of said second tubular shell is covered by a first polymeric sleeve comprised of a heat shrink tubing that is heated and shrunk in place, wherein the diameter of the shell mid-portion and first polymeric sleeve together is greater than the diameter of the shell distal portion such that said first polymeric sleeve limits direct contact between said first and second tubular shells;
   further wherein rotation of said second tubular member relative to said first tubular member causes the respective first and second cutting apertures to align and cooperatively resect tissue within a target site that is in contact with said apertures while said first polymeric sleeve forms a lubricious bearing between said first and second tubular shells.

2. The endoscopic cutting instrument of claim 1, wherein said second tubular member further comprises a middle portion that is covered by a second polymeric sleeve comprised of a heat shrink tubing that is heated and shrunk in place, such that said second polymeric sleeve prevents direct contact between said first and second tubular members and further limits the flexing of said second tubular member within said first tubular member and thus limits direct contact between the first and second cutting apertures.

3. The endoscopic cutting instrument of claim 2, wherein the diameter of the second tubular member mid-portion and second polymeric sleeve together is greater than the diameter of the distal end of said second tubular member.

4. The endoscopic cutting instrument of claim 2, wherein said second polymeric sleeve maintains the presence of a gap between the outer surface of said second tubular member and the inner surface of said first tubular member.

5. The endoscopic cutting instrument of claim 2, wherein said first and second polymeric sleeves are fabricated of a material selected from among PTFE, PEEK, polyolefin, and other suitable elastomeric polymeric materials.

6. The endoscopic cutting instrument of claim 1, wherein said first tubular shell comprises a closed-ended tube while said second tubular member comprises an open-ended tube.

7. The endoscopic cutting instrument of claim 1, wherein said first and second tubular members and said first and second tubular shells all comprise discrete components.

8. The endoscopic cutting instrument of claim 7, wherein said discrete first and second tubular shells are affixed to the respective distal ends of said discrete first and second tubular members by laser welding, brazing or other suitable means of permanent bonding.

9. The endoscopic cutting instrument of claim 1, wherein said first tubular member and said first tubular shell comprise a single integrated unit.

10. The endoscopic cutting instrument of claim 1, wherein first and second tubular members and first and second tubular shells are fabricated from the same metal alloy.

11. The endoscopic cutting instrument of claim 1, wherein first and second tubular members and first and second tubular shells are fabricated from different metal alloys.

12. The endoscopic cutting instrument of claim 1, wherein said inner assembly further comprises a central lumen that extends between the proximal end of said second tubular member and the distal end of said second tubular shell, wherein said central lumen is configured to aspirate resected tissue and/or supply an irrigant to the target site.

13. An endoscopic assembly comprising the endoscopic cutting instrument of claim 1 assembled onto a hub assembly comprising:

a. an inner hub comprising a conically tapered distal portion having a plurality of spaced slots disposed therein that form a plurality of spaced, distally projecting fingers disposed about a first central lumen, wherein said fingers are configured to grip a proximal end of said inner tubular member, further wherein said fingers form a first included angle; and
 b. a polymeric annular collar that is configured to slide over said projecting fingers gripping said proximal end of said inner tubular member, said collar having a conical inner surface complementary to that of the conically tapered distal portion of said inner hub including (i) a first conical portion of a second included angle that is approximately equivalent to said first included angle and (ii) a second conical portion having a distal-most diameter than is less than the distal-most diameter of said conical tubular portion;
 wherein said collar is assembled onto the projecting fingers such that deflection of the projecting fingers grips said proximal end of said tubular member.

14. A low-cost method of manufacturing the endoscopic cutting instrument of claim 1, said method comprising the steps of:

c. providing said inner and outer assemblies in which the distal ends of said elongate first and second members are affixed to the respective proximal ends of said first and second tubular shells
 d. applying, heating and shrinking said first polymeric sleeve to said mid-portion of said second tubular shell until the diameter of said mid-portion and said first polymeric sleeve together is greater than the diameter of the shell distal portion.

15. The method of claim 14, further comprising the step of:

e. assembling said outer and inner assemblies together by inserting said inner assembly within the central lumen of said outer assembly and sliding said inner assembly in the distal direction until said respective first and second cutting apertures align; wherein said first polymeric sleeve forms a lubricious bearing between said first and second tubular shells.

\* \* \* \* \*